(12) United States Patent
Kim et al.

(10) Patent No.: US 10,441,665 B2
(45) Date of Patent: *Oct. 15, 2019

(54) LIQUID FORMULATION OF LONG ACTING INSULINOTROPIC PEPTIDE CONJUGATE

(71) Applicant: HANMI PHARM. CO., LTD., Hwaseong-si, Gyeonggi-do (KR)

(72) Inventors: Hyun Uk Kim, Busan (KR); Hyung Kyu Lim, Hwaseong-si (KR); Sung Hee Hong, Suwon-si (KR); Dae Jin Kim, Hwaseong-si (KR); Sung Min Bae, Seongnam-si (KR); Se Chang Kwon, Seoul (KR)

(73) Assignee: HANMI PHARM. CO., LTD., Hwaseong-si (KR)

(*) Notice: Subject to any disclaimer, the term of this patent is extended or adjusted under 35 U.S.C. 154(b) by 54 days.

This patent is subject to a terminal disclaimer.

(21) Appl. No.: 15/714,556

(22) Filed: Sep. 25, 2017

(65) Prior Publication Data

US 2018/0015175 A1 Jan. 18, 2018

Related U.S. Application Data

(63) Continuation-in-part of application No. 14/416,223, filed as application No. PCT/KR2013/006670 on Jul. 25, 2013, now Pat. No. 9,801,950.

(30) Foreign Application Priority Data

Jul. 25, 2012 (KR) .................. 10-2012-0081476

(51) Int. Cl.
| | |
|---|---|
| A61K 39/00 | (2006.01) |
| A61K 38/26 | (2006.01) |
| C07K 16/00 | (2006.01) |
| C12P 21/08 | (2006.01) |
| A61K 47/68 | (2017.01) |
| C07K 16/42 | (2006.01) |
| C07K 16/28 | (2006.01) |
| C07K 16/06 | (2006.01) |
| A61K 9/08 | (2006.01) |
| C07K 14/575 | (2006.01) |
| C07K 14/605 | (2006.01) |
| A61K 47/26 | (2006.01) |
| A61K 39/395 | (2006.01) |
| C07K 19/00 | (2006.01) |
| G01N 33/50 | (2006.01) |

(52) U.S. Cl.
CPC .............. *A61K 47/68* (2017.08); *A61K 9/08* (2013.01); *A61K 39/39591* (2013.01); *A61K 47/26* (2013.01); *A61K 47/6811* (2017.08); *C07K 14/57563* (2013.01); *C07K 14/605* (2013.01); *C07K 16/065* (2013.01); *C07K 16/28* (2013.01); *C07K 16/4283* (2013.01); *C07K 19/00* (2013.01); *C07K 2317/50* (2013.01); *C07K 2319/30* (2013.01); *G01N 33/5047* (2013.01)

(58) Field of Classification Search
None
See application file for complete search history.

(56) References Cited

U.S. PATENT DOCUMENTS

| | | | |
|---|---|---|---|
| 5,545,618 | A | 8/1996 | Buckley et al. |
| 6,924,264 | B1 | 8/2005 | Prickett et al. |
| 2006/0210614 | A1 | 9/2006 | Quay et al. |
| 2008/0124347 | A1 | 5/2008 | Kim et al. |
| 2008/0249018 | A1 | 10/2008 | Kolterman et al. |
| 2008/0318865 | A1 | 12/2008 | Juul-Mortensen |
| 2009/0181037 | A1 | 7/2009 | Heavner |
| 2009/0181912 | A1 | 7/2009 | Wang et al. |
| 2009/0238838 | A1 | 9/2009 | Kim et al. |
| 2010/0196405 | A1 | 8/2010 | Ng |
| 2012/0252724 | A1 | 10/2012 | Schoettle et al. |
| 2015/0025227 | A1 | 1/2015 | Jung et al. |

FOREIGN PATENT DOCUMENTS

| | | |
|---|---|---|
| CN | 1723219 A | 1/2006 |
| CN | 101730523 A | 6/2010 |
| JP | 2010-533197 A | 10/2010 |
| JP | 2011-503000 A | 1/2011 |
| JP | 2011-505355 A | 2/2011 |

(Continued)

OTHER PUBLICATIONS

Parkes DG et al., "Insulinotropic actions of exendin-4 and glucagon-like peptide-1 in vivo and in vitro," Metabolism, May 2001, pp. 583-589, vol. 50, No. 5 (Abstract).

Alfred Aziz et al., "Exendin-4, a GLP-1 Receptor Agonist, Modulates the Effect of Macronutrients on Food Intake by Rats," J. Nutr., 2002, pp. 990-995, vol. 132.

Josephine M. Egan et al., "The Insulinotropic Effect of Acute Exendin-4 Administered to Humans: Comparison of Nondiabetic State to Type 2 Diabetes," Journal of Clinical Endocrinology & Metabolism, 2002, pp. 1282-1290, vol. 87, No. 3.

(Continued)

*Primary Examiner* — Shulamith H Shafer
(74) *Attorney, Agent, or Firm* — Sughrue Mion, PLLC

(57) ABSTRACT

Provided are a liquid formulation of long-acting insulinotropic peptide conjugate, containing a pharmaceutically effective amount of long-acting insulinotropic peptide conjugate consisting of a physiologically active peptide, insulinotropic peptide, and an immunoglobulin Fc region; and an albumin-free stabilizer, wherein the stabilizer comprises a buffer, a sugar alcohol, and a non-ionic surfactant, and a method for preparing the formulation. For the purpose of preventing microbial contamination, a preservative may be added. The liquid formulation of the present invention is free of human serum albumin and other potentially hazardous factors to body, having no risk of viral contamination, and thus can provide excellent storage stability for insulinotropic peptide conjugates at high concentration.

33 Claims, 3 Drawing Sheets

(56) References Cited

FOREIGN PATENT DOCUMENTS

| | | | |
|---|---|---|---|
| KR | 10-0567902 B1 | 4/2006 | |
| KR | 10-0725315 B1 | 6/2007 | |
| KR | 10-2007-0089187 A | 8/2007 | |
| KR | 10-2008-0064750 A | 7/2008 | |
| KR | 10-2009-0008151 A | 1/2009 | |
| KR | 10-2009-0033906 A | 4/2009 | |
| KR | 10-1058290 B1 | 8/2011 | |
| WO | 2006/076471 A2 | 7/2006 | |
| WO | 2009/009562 A2 | 1/2009 | |
| WO | 2009/059278 A1 | 5/2009 | |
| WO | 2009/069983 A2 | 6/2009 | |
| WO | 2009069983 A2 | 6/2009 | |
| WO | 2011/090306 A2 | 7/2011 | |
| WO | 2012/057525 A2 | 5/2012 | |

OTHER PUBLICATIONS

Orville G. Kolterman et al., "Synthetic Exendin-4 (Exenatide) Significantly Reduces Postprandial and Fasting Plasma Glucose in Subjects with Type 2 Diabetes," Journal of Clinical Endocrinology & Metabolism, 2003, pp. 3082-3089, vol. 88, No. 7.
Mark S. Fineman et al., "Effect on Glycemic Control of Exenatide (Synthetic Exendin-4) Additive to Existing Metformin and/or Sulfonylurea Treatment in Patients With Type 2 Diabetes," Diabetes Care, Aug. 2003, pp. 2370-2377, vol. 26, No. 8.
Deacon CF et al., "Dipeptidyl peptidase IV inhibition potentiates the insulinotropic effect of glucagon-like peptide 1 in the anesthetized pig.," Diabetes, May 1998, pp. 764-769, vol. 47, No. 5 (Abstract).
Burcelin R. et al., "Acute intravenous leptin infusion increases glucose turnover but not skeletal muscle glucose uptake in ob/ob mice.," Diabetes, Jun. 1999, pp. 1264-1269, vol. 48, No. 6 (Abstract).
Gallwitz B. et al., "GLP-1-analogues resistant to degradation by dipeptidyl-peptidase IV in vitro.," Regulatory Peptides, Jan. 29, 2000, pp. 103-111, vol. 86 (Abstract).
Geigert J., "Overview of the stability and handling of recombinant protein drugs.," J. Parenteral Sci. Tech., Sep.-Oct. 1989, pp. 220-224, vol. 43, No. 5 (Abstract).
Wei Wang, "Instability, stabilization, and formulation of liquid protein pharmaceuticals," International Journal of Pharmaceutics, 1999, pp. 129-188, vol. 185.
Norde W., "Adsorption of proteins from solution at the solid-liquid interface.," Adv. Colloid Interface Sci., Sep. 1986, pp. 267-340, vol. 25, No. 4 (Abstract).
Edward Tarelli et al., "Recombinant Human Albumin as a Stabilizer for Biological Materials and for the Preparation of International Reference Reagents," Biologicals, 1998, pp. 331-346, vol. 26.
International Searching Authority, International Search Report of PCT/KR2013/006670 dated Nov. 18, 2013.
International Searching Authority, Written Opinion of the International Searching Authority of PCT/KR2013/006670 dated Nov. 18, 2013.
European Patent Office, Communication dated Feb. 18, 2016, issued in counterpart European Application No. 13823275.6.
Communication dated May 20, 2016, from the State Intellectual Property Office of People's Republic of China in counterpart application No. 201380039383.7.
Japan Patent Office; Communication dated Apr. 5, 2017, in corresponding Application No. 2015-524183.

[Figure 1]
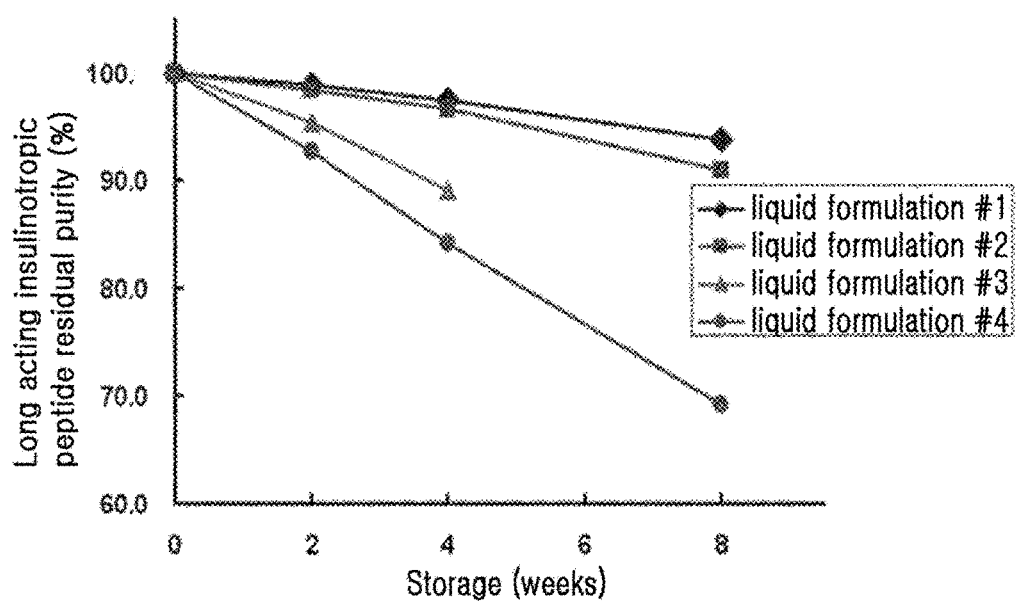

[Figure 2]
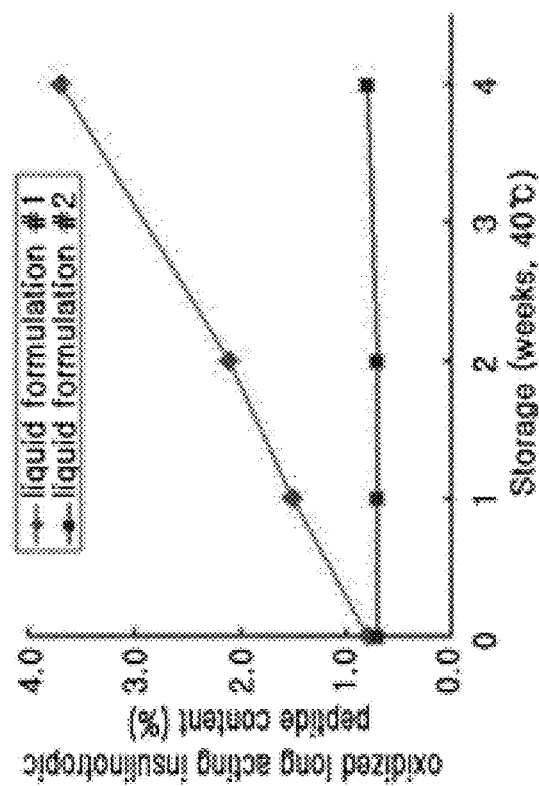
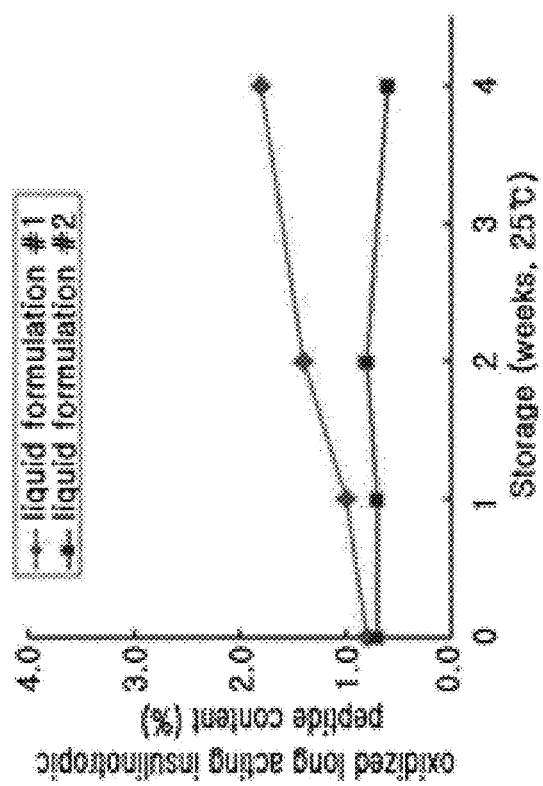

[Figure 3]
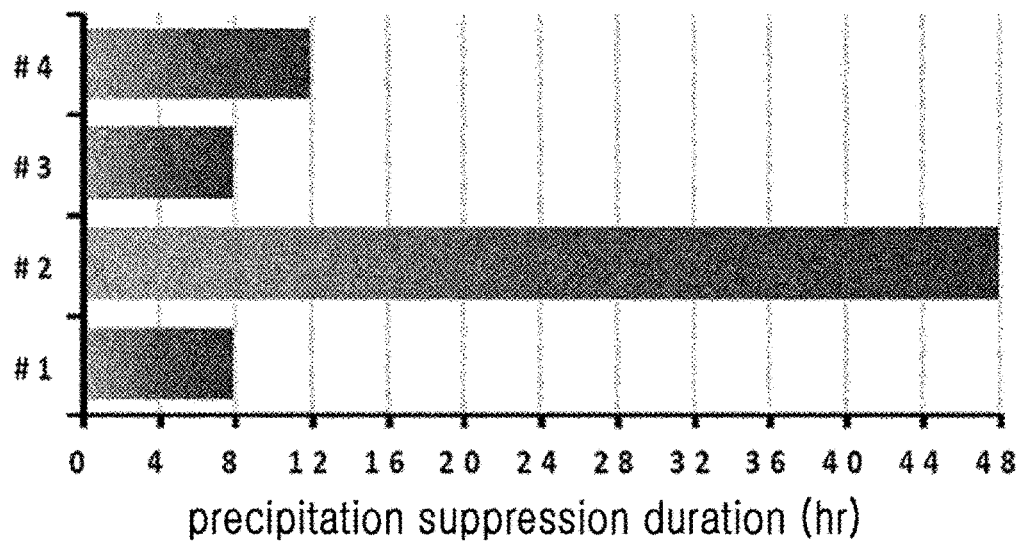
[Figure 4]
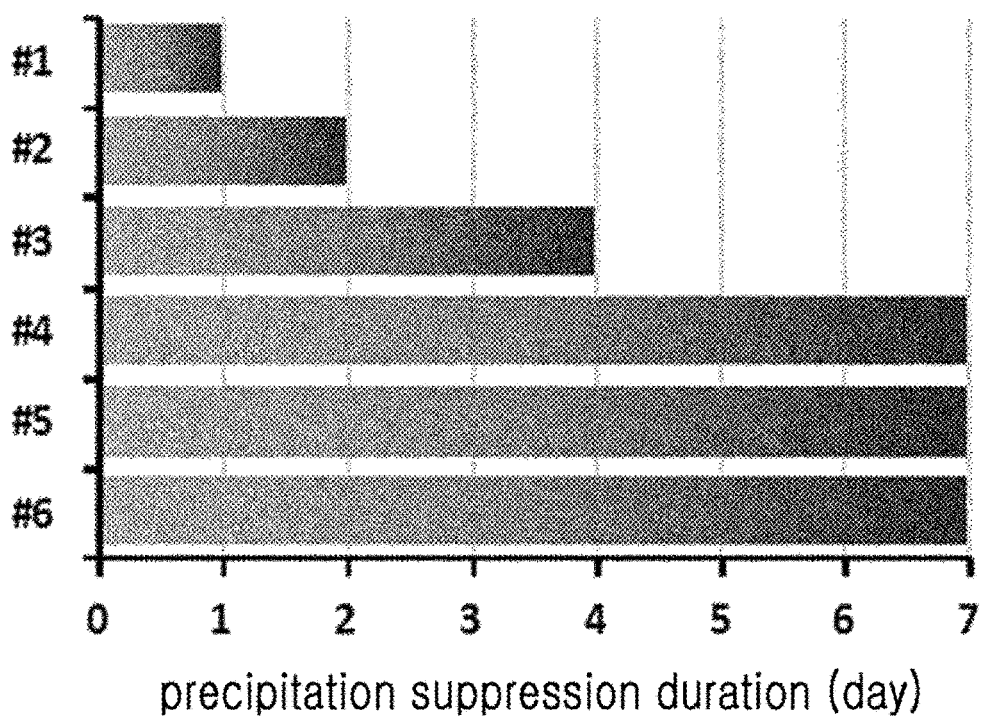

LIQUID FORMULATION OF LONG ACTING INSULINOTROPIC PEPTIDE CONJUGATE

CROSS REFERENCE TO RELATED APPLICATIONS

The instant application is a continuation-in-part of application Ser. No. 14/416,223 (allowed) filed Jan. 21, 2015, which is a 371 application of PCT/KR2013/006670 filed Jul. 25, 2013, which claims priority from Korean Patent Application No. 10-2012-0081476 filed Jul. 25, 2012, of which entire contents are incorporated herein by reference.

TECHNICAL FIELD

The present invention relates to a liquid formulation of long-acting insulinotropic peptide conjugate, comprising a pharmaceutically effective amount of long-acting insulinotropic peptide conjugate wherein a physiologically active peptide which is an insulinotropic peptide is linked to an immunoglobulin Fc region; and an albumin-free stabilizer, wherein the stabilizer comprises a buffer, a sugar alcohol, and a non-ionic surfactant, and a method for preparing the formulation.

BACKGROUND ART

Diabetes is a disease derived from multiple pathogenetic factors and generally there are two types of diabetes. Patients with type I diabetes or insulin-dependent diabetes mellitus (IDDM) barely produce or cannot produce insulin which is a hormone regulating a use of carbohydrates. And patients with type II diabetes or non-insulin-dependent diabetes mellitus (NIDDM) show the same or increased plasma insulin level compared to patients with no diabetes. However, the type II diabetes patients develop a resistance to insulin-stimulated-glucose and lipid metabolism in main insulin-sensitive tissues, i.e. muscle, liver, and fat tissue. Although plasma insulin level can be increased, it is not sufficient to overcome the significant insulin resistance, thereby causing hyperglycemia. Continued or unregulated hyperglycemia is associated with increased early morbidity rate and mortality rate. Often times, abnormal increase in sugar level is directly and indirectly related to the metabolic and hemodynamic changes in the diseases associated with the metabolisms of lipid, lipoprotein, apolipoprotein, and others. For example, patients of type II diabetes mellitus especially have a high risk of developing a coronary heart disease, stroke, peripheral vascular disease, hypertension, nephropathy, and neuropathy as well as giant hemangioma and microvascular complications.

The currently used therapies for treating type II diabetes include administration of foreign insulin, oral administration of drug, diet therapy, and exercise therapy. In 2005, exenatide (Exendin-4: Byetta) was approved by FDA as a supplemental therapy for type II diabetes patients who could not get the appropriate glucose regulation even with taking metformin and/or sulphonylurea.

Exenatide (exendin-4) is a strong GLP-1 receptor agonist and is produced in the salivary gland of lizard. Exendin-4 shows affinity to insulin, suppress food intake and gastric emptying, and show affinity to (β-cells in rodents (Parks et al., Metabolism. 50: 583-589, 2001; Aziz and Anderson, J. Nutr. 132: 990-995, 2002; and Egan et al., J. Clin. Endocrinol. Metab. 87: 1282-1290, 2002). In addition, as glycine is present at position 2 of the N-terminal of exidine-4, it is not a substrate for DPPIV unlike GLP-1. Disadvantage of using exenatide is a short half-life (t½) which is only 2 to 4 hours, and thus it has to be injected twice per day (Kolterman et al., J. Clin. Endocrinol. Metab. 88: 3082-3089, 2003 and Fineman et al., Diabetes Care. 26: 2370-2377, 2003).

Peptides like the above-described exenatide are easily denatured or degraded by proteases in the body due to low stability and lose activity. Also, the size of exenatides is relatively small and thus easily removed by the kidney. Hence, drugs containing peptides as pharmaceutically active ingredients have to be frequently administered to patients in order to maintain the target serum level and titer thereof. Mostly, the peptide drugs are administered to the patients in the form of injection and at high frequency to maintain the serum level of physiologically active peptide, but this causes a lot of pain in patients.

There have been many attempts to solve these problems, and one of them was the delivering of a peptide drug into the body through oral or nasal inhalation by increasing the biomembrane permeability of the peptide drug. However, this method has significantly low efficiency for delivering the peptide into the body compared to injections. Therefore, there are still many limitations in maintaining the activity of peptide drug in vivo at the required level.

Meanwhile, there have been continuous attempts to maximize therapeutic effects of drug by improving the stability of peptide drug in blood and maintaining a high drug level in blood for a long period of time. These long-acting formulations of peptide drugs should promote an increased stability of peptide drug and also maintain a sufficiently high titer of drug itself without inducing immune responses in patients.

As a method for stabilizing peptides and preventing peptide degradation by protease, there have been many attempts to modify a specific amino acid sequence sensitive to protease. For example, GLP-1 (7-37 or 7-36 amide) that is effective in treating type II diabetes by reducing blood glucose level has a half-life as short as below 4 minutes (Kreymann et al., 1987). The short half-life is due to loss of titer of GLP-1 through peptide cleavage between amino acid No. 8 (Ala) and No. 9 (Asp) of GLP-1 by dipeptidyl pepdidase IV (DPP IV). Thus, there have been many studies on developing GLP-1 derivatives having resistance to DPP IV, and in these studies, Ala$^8$ was substituted by Gly (Deacon et al., 1998; Burcelin et al., 1999), or by Leu or D-Ala (Xiao et al., 2001) for increasing resistance to DPP IV while maintaining the peptide activity. Also, the N-terminal amino acid of GLP-1, His$^7$, is an important amino acid for GLP-1 activity and also a target of DPP IV, and thus in U.S. Pat. No. 5,545,618, the N-terminal was substituted by alkyl group or acyl group. Likewise, in Gallwitz et al., His$^7$ was N-methylated or alpha-methylated, or the whole His was substituted by imidazole for increasing peptide resistance to DPP IV while maintaining bioactivity (Baptist Gallwitz, et al., Regulatory Peptides 86, 103-111, 2000).

Besides these variants, exenatide (exendin-4, U.S. Pat. No. 5,424,686) which is a GLP-1 derivative purified from a salivary gland of glia monster has a resistance to DPP IV and a higher bioactivity than GLP-1, thereby having 2 to 4 hour-long half-life in the body which is a lot longer than that of GLP-1. However, a sufficient in vivo duration of bioactivity cannot be derived solely by increasing the peptide resistance to DPP IV. For example, the currently available exendin-4 (exenatide) has to be administered twice a day to patients through injections, which brings undue burden to the patients.

A limitation of these insulinotropic peptides is in that the size of peptide is too small to get collected in the kidney and thus it is easily lost outside of the body. Therefore, in order to prevent the loss of peptide in kidney, a highly soluble macromolecule such as polyethylene glycol (PEG) has been attached to the surface of peptide.

PEG binds to a specific site or various sites of a target peptide non-specifically and increases the molecular weight of the peptide, which then prevents the loss of peptide in kidney and hydrolysis of peptide, without causing side effects. For example, WO2006/076471 discloses that by attaching PEG to a B-type natriuretic peptide (BNP), which activates production of cGMP by binding to NPR-A and reduces intra-arterial blood pressure, thereby being effective as therapeutic agent for congestive heart failure, the bioactivity of BNP can be maintained. Likewise, U.S. Pat. No. 6,924,264 describes a method for increasing the in vivo durability of exidine-4 by attaching PEG to lysine residue of an exidine-4. However, while these methods can extend the in vivo durability of a peptide drug by increasing the PEG molecular weight, the titer of the peptide drug gets remarkably reduced as the PEG molecular weight increases, and also the PEG reactivity with the peptide is reduced, thereby reducing yield.

As another method for increasing the in vivo stability of physiologically active peptide, a method for producing a fusion protein, where the genes for peptide and physiologically active protein are linked through genetic recombination and the cells transformed with the recombinant gene are cultured, has been developed. For example, a fusion protein producing exendin-4 which is fused to transferrin (Tf) through polypeptide linker was previously reported (Korean Patent Application No. 10-2009-7003679). Also, as a method for using immunoglobulin, a fusion protein of GLP-1 derivative where GLP-1 derivative is fused to IgG4 Fc was also disclosed before (Korean Patent Application No. 10-2007-7014068).

Recently, as a long-acting protein and peptide drug formulation which can promote a minimal reduction in activity and an increased stability, a conjugate generated by combining immunoglobulin Fc region, non-peptidyl polymer, and physiologically active polypeptide is disclosed in Korean Patent Registration No. 10-0567902 (Physiologically active polypeptide conjugate having improved in vivo durability) and Korean Patent Registration No. 10-0725315 (Protein complex using an immunoglobulin fragment and method for the preparation thereof).

Through the above method, insulinotropic peptide may be applied as a physiologically active polypeptide for preparing a long-acting insulinotropic peptide conjugate (Korean Patent Registration No. 10-2008-0001479). To manufacture the drug comprising a long-acting insulinotropic peptide conjugate, it is essential to prevent physiochemical changes such as heat-induced denaturation, aggregation, adsorption, or hydrolysis caused by light, heat, or impurities in additives during storage and delivery processes while maintaining in vivo efficacy. In particular, a long-acting insulinotropic peptide conjugate has larger volume and molecular weight compared to the insulinotropic peptide itself, and thus it is hard to stabilize.

Generally, proteins and peptides have a short half-life and can undergo denaturation, such as aggregation of monomers, precipitation by aggregation, and adsorption to the surface of container, when exposed to unsuitable temperatures, water-air interface, high pressure, physical or mechanical stress, organic solvents, and microbial contamination. The denatured proteins and peptides lose their inherent physiochemical properties and physiological activity. Since protein denaturation is irreversible in most cases, the denatured proteins and peptides cannot recover their inherent properties. Also, it is likely that the proteins are unstable and easily affected by outside factors such as temperature, humidity, oxygen, ultraviolet rays, and thus they undergo physical or chemical changes including aggregation, polymerization, or oxidation, thereby losing activity.

Also, the adsorbed proteins and peptides are apt to aggregate as they denature, and when the aggregated proteins and peptides are introduced into the body, they may cause antibody formation. Thus sufficiently stable proteins and peptides must be administered. In this regard, there have been various methods developed to prevent the denaturation of protein and peptide in solution (John Geigert, J. Parenteral Sci. Tech., 43, No5, 220-224, 1989, David Wong, Pharm. Tech. October, 34-48, 1997, Wei Wang., Int. J. Pharm., 185, 129-188, 1999, Willem Norde, Adv. Colloid Interface Sci., 25, 267-340, 1986, Michelle et al., Int. J. Pharm. 120, 179-188, 1995).

For producing some of protein and peptide drugs, a freeze-drying process has been used to solve stability issue. However, this process is inconvenient in that freeze-dried products have to be dissolved in solvents for injection again before use, and it requires a large-scale investment such as using a large number of freeze-driers since the freeze-drying process is involved in the manufacturing process. Alternatively, powdering method using a spray drier has also been used. However this method has low economical value due to low product yield and may give negative effect on product stability since the proteins are exposed to high temperature.

As an alternative approach to resolve these limitations, other studies tried to add stabilizers to the protein and peptide in solution to prevent physiochemical changes of protein drug while maintaining in vivo efficacy thereof during long-term storage. A type of protein, human serum albumin, has been widely used as a stabilizer for various protein drugs, and the efficacy thereof has been approved (Edward Tarelli et al., Biologicals (1998) 26, 331-346).

Purification of human serum albumin involves inactivation of biological contaminants such as mycoplasma, prions, bacteria, and viruses, or screening or inspecting of one or more biological contaminants or pathogens, but even with these processes, those contaminants may not be completely removed or inactivated. Thus, patients may be exposed to these biological contaminants or pathogens when administered with human serum albumin. For example, although screening process involves the inspection of certain virus in the blood sample of donor, the inspection process is not always reliable and cannot detect certain viruses that are present in small number.

Due to their chemical differences, different proteins may be gradually inactivated at different rates under different conditions during storage. That is, the extension of storage term by a stabilizer is not the same for different proteins. For this reason, the suitable ratio, concentration, and type of stabilizers that are used to improve storage stability of proteins vary depending on the physiochemical properties of a target protein. Furthermore, when different stabilizers are used together, they may induce adverse effects different from those desired, due to competitive interaction and side effects. Also, during storage, the property of stored protein or concentration thereof can change, thereby causing different effects.

Therefore, it takes a lot of efforts and cautions to stabilize proteins in solution. Particularly, a long-acting insulinotropic peptide conjugates having improved in vivo durability and stability has a form of insulinotropic peptide, combined with immunoglobulin Fc region, and thus it has significantly different molecular weight and volume compared to general insulinotropic peptide. Therefore, a special composition is required for stabilizing the protein. Also, an insulinotropic peptide and an immunoglobulin Fc region are physiochemically different peptide or protein, and thus they have to be stabilized concurrently. However, as described above, different peptides or proteins may be gradually inactivated at different rates under different conditions during storage due to the physiochemical difference thereof. Also, when the stabilizers that are suitable for each of peptide or protein are used together, they may induce adverse effects different from desired effects, due to competitive interaction and side effects. Therefore, as for a long-acting insulinotropic peptide conjugate, it is highly difficult to find a stabilizer composition that can stabilize both an insulinotropic peptide, and an immunoglobulin Fc region concurrently.

Recently, a formulation of protein and peptide that can be used repeatedly for the patient's convenience has been developed. However, the multiple-use formulation must contain a preservative to prevent the microbial contamination after repeated administrations and prior to disposal. The multiple-use formulation containing preservative has a few advantages compared to a single-use formulation. For example, as for a single-use formulation, a large amount of drug is wasted depending on the difference in dosage. But by using a multiple-use formulation, the amount of product wasted can be reduced. Furthermore, the multiple-use formulation can be used several times without concerning about microbial growth within certain period, and since it can be supplied in a single container, packing can be minimized, leading to economic benefits.

However, use of preservative may affect the protein stability. The most well-known problem in use of preservative is precipitation issue. Precipitation of protein can reduce therapeutic effects of drug and when administered to the body it can induce unexpected immune response. Therefore, it is critical to select a type and appropriate concentration of preservative that maintain the ability to prevent microbial contamination while not affecting protein stability.

In an effort to provide a stable liquid formulation of long-acting insulinotropic peptide conjugate that can store the long-acting insulinotropic peptide conjugate without the risk of viral contamination for a long period of time, the present invention found that a formulation that enhances the stability of long-acting insulinotropic peptide conjugate could be provided by using a stabilizer comprising a buffer, a sugar alcohol, and a non-ionic surfactant, or additionally methionine, and that the formulation can be used multiple times when a preservative is further comprised in the formulation, thereby completing a cost-effective and stable liquid formulation.

DISCLOSURE

Technical Problem

One object of the present invention is to provide a liquid formulation of long-acting insulinotropic peptide conjugate, comprising a pharmaceutically effective amount of long-acting insulinotropic peptide conjugate wherein a physiologically active peptide, i.e., insulinotropic peptide is linked to an immunoglobulin Fc region; and an albumin-free stabilizer, wherein the stabilizer comprises a buffer, a sugar alcohol, and a non-ionic surfactant.

Another object of the present invention is to provide a liquid formulation of long-acting insulinotropic peptide conjugate for multiple administrations, further comprising a preservative in addition to the insulinotropic peptide conjugate and albumin-free stabilizer.

Another object of the present invention is to provide a method for preparing the liquid formulation of long-acting insulinotropic peptide conjugate.

Technical Solution

In order to achieve the above objects, an aspect of the present invention provides a liquid formulation of a long-acting insulinotropic peptide conjugate.

In a specific embodiment, the present invention relates to a liquid formulation of a long-acting insulinotropic peptide conjugate, comprising a pharmaceutically effective amount of the long-acting insulinotropic peptide conjugate wherein an insulinotropic peptide is linked to an immunoglobulin Fc region; and an albumin-free stabilizer, wherein the stabilizer comprises a buffer, a sugar alcohol, and a non-ionic surfactant.

In the liquid formulation according to the previous embodiment, the insulinotropic peptide may be glucagon-like peptide-1, glucagon-like peptide-2, exendin-3, exendin-4, or imidazo-acetyl exendin-4.

In the liquid formulation according to any one of the previous embodiments, the formulation has a pH of about 5.2 to about 7.0.

In the liquid formulation according to any one of the previous embodiments, the non-ionic surfactant has a concentration of about 0.001% (w/v) to about 0.05% (w/v).

In the liquid formulation according to any one of the previous embodiments, the immunoglobulin Fc region is an Fc region derived from IgG, IgA, IgD, IgE, or IgM.

In the liquid formulation according to any one of the previous embodiments, the immunoglobulin Fc region is a hybrid of domains of different origins derived from immunoglobulins selected from the group consisting of IgG, IgA, IgD, IgE, and IgM.

In the liquid formulation according to any one of the previous embodiments, the immunoglobulin Fc region is a dimer or multimer consisting of single-chain immunoglobulins composed of domains of the same origin.

In the liquid formulation according to any one of the previous embodiments, the immunoglobulin Fc region is an IgG4 Fc region.

In the liquid formulation according to any one of the previous embodiments, the immunoglobulin Fc region is a human aglycosylated IgG4 Fc region.

In the liquid formulation according to any one of the previous embodiments, the insulinotropic peptide is linked to the immunoglobulin Fc region via a non-peptidyl polymer or a fusion protein.

In the liquid formulation according to any one of the previous embodiments, the non-peptidyl polymer is a polyethylene glycol.

In the liquid formulation according to any one of the previous embodiments, the non-peptidyl polymer is selected from the group consisting of a biodegradable polymer; a lipid polymer; chitins; hyaluronic acid; and a combination thereof, wherein said biodegradable polymer is selected from the group consisting of polypropylene glycol, a copolymer of ethylene glycol and propylene glycol, polyoxyethylated polyol, polyvinyl alcohol, polysaccharide, dextran, polyvinyl ethyl ether, polylactic acid, and polylactic-glycolic acid.

In the liquid formulation according to any one of the previous embodiments, the pharmaceutically effective amount of the long-acting insulinotropic peptide conjugate has a concentration of about 0.5 mg/mL to about 150 mg/mL.

In the liquid formulation according to any one of the previous embodiments, the pharmaceutically effective amount of the long-acting insulinotropic peptide conjugate has a concentration of about 4.0 mg/mL to about 50 mg/mL.

In the liquid formulation according to any one of the previous embodiments, the sugar alcohol is one or more selected from the group consisting of mannitol, sorbitol, and sucrose.

In the liquid formulation according to any one of the previous embodiments, a concentration of the sugar alcohol is about 3% (w/v) to about 15% (w/v) based on a total volume of the liquid formulation.

In the liquid formulation according to any one of the previous embodiments, the buffer is a citrate buffer, an acetate buffer, or a histidine buffer.

In the liquid formulation according to any one of the previous embodiments, the buffer is a citrate buffer.

In the liquid formulation according to any one of the previous embodiments, a concentration of the citrate is about 10 mM to about 100 mM based on a total volume of the liquid formulation.

In the liquid formulation according to any one of the previous embodiments, the citrate is present in a form of citric acid monohydrate.

In the liquid formulation according to any one of the previous embodiments, the pH range of the formulation is about 5.2 to about 6.0.

In the liquid formulation according to any one of the previous embodiments, the pH range of the formulation is about 5.4 to about 7.0.

In the liquid formulation according to any one of the previous embodiments, the pH of the formulation is adjusted by using HCl and/or NaOH.

In the liquid formulation according to any one of the previous embodiments, the non-ionic surfactant is polysorbate 80 or polysorbate 20.

In the liquid formulation according to any one of the previous embodiments, the stabilizer further comprises methionine.

In the liquid formulation according to any one of the previous embodiments, a concentration of the methionine is about 0.005% (w/v) to about 0.1% (w/v) based on a total volume of the liquid formulation.

In the liquid formulation according to any one of the previous embodiments, the stabilizer further comprises one or more substances selected from the group consisting of a sugar, a polyalcohol, and an amino acid.

In the liquid formulation according to any one of the previous embodiments, the liquid formulation further comprises one or more preservatives selected from the group consisting of m-cresol, phenol, and benzyl alcohol.

In the liquid formulation according to any one of the previous embodiments, a concentration of the one or more preservatives is 0.001% (w/v) to 1% (w/v) based on a total volume of the liquid formulation.

In the liquid formulation according to any one of the previous embodiments, the preservative is m-cresol.

In the liquid formulation according to any one of the previous embodiments, the liquid formulation comprises a pharmaceutically effective amount of the long-acting insulinotropic peptide conjugate wherein an insulinotropic peptide is linked to an immunoglobulin Fc region via polyethylene glycol; and an albumin-free stabilizer, wherein the stabilizer comprises citrate buffer, mannitol, and polysorbate 20, wherein, the insulinotropic peptide is glucagon-like peptide-1, glucagon-like peptide-2, exendin-3, exendin-4, or imidazo-acetyl exendin-4; the formulation has a pH of about 5.2 to about 7.0; the non-ionic surfactant has a concentration of about 0.001% (w/v) to about 0.05% (w/v).

In the liquid formulation according to any one of the previous embodiments, the stabilizer further comprises methionine.

In a specific embodiment, the present invention relates to a multiple-use liquid formulation of a long-acting insulinotropic peptide conjugate, the multiple-use liquid formulation comprising a pharmaceutically effective amount of the long-acting insulinotropic peptide conjugate wherein an insulinotropic peptide is linked to an immunoglobulin Fc region; an albumin-free stabilizer, wherein the stabilizer comprises a buffer, a sugar alcohol, and a non-ionic surfactant; and one or more preservatives selected from the group consisting of m-cresol, phenol, and benzyl alcohol, wherein the insulinotropic peptide is glucagon-like peptide-1, glucagon-like peptide-2, exendin-3, exendin-4, or imidazo-acetyl exendin-4; wherein the formulation has a pH of about 5.2 to about 7.0; and wherein the non-ionic surfactant has a concentration of about 0.001% (w/v) to about 0.05% (w/v).

In a specific embodiment, the present invention relates to a liquid formulation of a long-acting insulinotropic peptide conjugate, comprising:

about 4 mg/mL, about 8.0 mg/mL, or about 12.0 mg/mL of the long-acting insulinotropic peptide conjugate wherein an insulinotropic peptide is linked to an immunoglobulin Fc region via polyethylene glycol;

about 4.203 mg/mL citric acid monohydrate;

about 0.1 mg/mL L-methionine;

about 0.05 mg/mL polysorbate 20; and about 40 mg/mL D-mannitol;

wherein the formulation has a pH of about 5.6, and the pH of the formulation is adjusted by using NaOH; and the insulinotropic peptide is imidazo-acetyl exendin-4.

Still another aspect of the present invention provides a method for preparing the liquid formulation.

In a specific embodiment, the method comprises mixing a long-acting insulinotropic peptide conjugate wherein an insulinotropic peptide is linked to an immunoglobulin Fc region with a stabilizer comprising a buffer, a sugar alcohol, and a non-ionic surfactant.

In the method according to the previous embodiment, the insulinotropic peptide is glucagon-like peptide-1, glucagon-like peptide-2, exendin-3, exendin-4, or imidazo-acetyl exendin-4.

In the method according to any one of the previous embodiments, the buffer has a pH of about 5.2 to about 7.0.

In the method according to any one of the previous embodiments, the non-ionic surfactant has a concentration of about 0.001% (w/v) to about 0.05% (w/v).

In the method according to any one of the previous embodiments, the stabilizer further comprises methionine and/or a preservative.

Advantageous Effects

As the liquid formulation of long-acting insulinotropic peptide conjugate of the present invention comprises a buffer, a sugar alcohol, and a non-ionic surfactant, or additionally methionine, but is free of human serum albumin and other potentially hazardous factors to body, therefore there is no risk of viral contamination. Also, it can provide excellent storage stability for a long-acting insulinotropic peptide conjugate which comprises an insulinotropic peptide and an immunoglobulin Fc region, thereby having higher molecular weight and enhanced in vivo duration of physiological activity compared to the wild-type protein. Such liquid formulation of the present invention can provide excellent storage stability with simple formulation and provide the peptide drug more cost-effectively compared to other stabilizer and freeze-drier. If a preservative is added to the formulation, the formulation can be used multiple times. Also, the present formulation can retain the protein activity in the body for a longer period compared to a conventional insulinotropic peptide formulation, and thus it can be used as an effective drug formulation.

DESCRIPTION OF DRAWINGS

FIG. 1 is a graph showing the RP-HPLC analysis of the peptide stability in the finally selected liquid formulation at a pH of 5.2 (Liquid Formulation #1), the liquid formulation prepared by applying a long-acting insulinotropic peptide conjugate to a stabilizer composition of liquid formulation of commercially available insulinotropic peptide drug, exenatide, i.e., exendin-4 (Byetta) (Liquid Formulation #2), the liquid formulation prepared by applying a long-acting insulinotropic peptide conjugate to a stabilizer composition of liquid formulation of immunoglobulin fusion protein drug, etanercept (TNFR-Fc fusion protein, ENBREL) (Liquid Formulation #3), and a control group (Liquid Formulation #4) which were all stored at 25±2° C. for 8 weeks.

FIG. 2 is a graph showing the RP-HPLC analysis of the proportion of oxidized long-acting insulinotropic peptide conjugate in the finally selected liquid formulation at a pH of 5.2 lacking methionine (Liquid Formulation #1) and in the liquid formulation at a pH 5.2 comprising methionine (Liquid Formulation #2) while storing them at 25±2° C. and at 40±2° C. for 4 weeks.

FIG. 3 shows the results of monitoring the occurrence of precipitation in the compositions of long-acting insulinotropic peptide conjugate according to Table 18 with naked eyes at 40° C. for 48 hours. The duration of the absence of precipitation indicates the time during which protein precipitation did not occur after storing the peptide.

FIG. 4 shows the results of monitoring the occurrence of precipitation in the compositions of long-acting insulinotropic peptide conjugate according to Table 19 with naked eyes at 40° C. for 7 days. The duration of the absence of precipitation indicates the time during which protein precipitation did not occur after storing the peptide.

BEST MODE

The specific details of the present invention may be explained as follows. In particular, the explanations and embodiments disclosed in the present invention may be applied to other explanations and embodiments, respectively. That is, all combinations of various elements disclosed in the present invention belong to the scope of the present invention. Additionally, the scope of the present invention should not be limited by the specific descriptions described herein below.

Additionally, those of ordinary skill in the art may be able to recognize or confirm, using only conventional experimentation, many equivalents to the particular aspects of the invention described in this application. Furthermore, it is also intended that these equivalents be included in the present invention.

As one aspect, the present invention provides a liquid formulation of long-acting insulinotropic peptide conjugate, comprising a pharmaceutically effective amount of long-acting insulinotropic peptide conjugate wherein an insulinotropic peptide is linked to an immunoglobulin Fc region; and an albumin-free stabilizer, wherein the stabilizer comprises a buffer, a sugar alcohol, and a non-ionic surfactant.

In addition, the present invention provides a liquid formulation of long-acting insulinotropic peptide conjugate for multiple administrations, further comprising a preservative in addition to the insulinotropic peptide conjugate and albumin-free stabilizer.

As used herein, "long-acting insulinotropic peptide conjugate" refers to a conjugate wherein a physiologically active insulinotropic peptide comprising a derivative, variant, precursor, and fragment and an immunoglobulin Fc region are linked, and it may further refer to a conjugate having increased in vivo duration of physiological activity compared to a wild-type insulinotropic peptide.

As used herein, the term "long-acting" refers to an enhancement of duration of physiological activity compared to that of a wild-type. The term "conjugate" refers to the form wherein an insulinotropic peptide and immunoglobulin Fc region are combined.

The insulinotropic peptide used in the present invention has a function of secreting insulin and it stimulates the synthesis and expression of insulin in pancreatic β-cells. The type of insulinotropic peptide includes precursor, agonist, derivatives, fragments, and variants. Preferably, the insulinotropic peptide may be a glucagon like peptide-1 (GLP-1), a glucagon like peptide-2 (GLP-2), exendin-3, exendin-4, and imidazoacetyl (CA) exendin-4, and more preferably, imidazoacetyl (CA) exendin-4. Any insulinotropic peptide, either native or recombinant, may be used and preferably it is a recombinant insulinotropic peptide generated by using E. coli as a host cell. As long as its biological activity is not significantly affected, any derivatives thereof, which are generated by substitution, deletion, or insertion of amino acids, may be used in the present invention.

The sequence of the insulinotropic peptide may be obtained from known database such as GenBank of NCBI, and it can have 70% or more, preferably 80% or more, more preferably 90% or more, and even more preferably 95% or more, and most preferably 98% or more sequence homology with a wild-type protein, as long as it demonstrates the activity of an insulinotropic peptide.

Furthermore, the immunoglobulin Fc useful of the present invention may be a human immunoglobulin Fc or its closely related analog or immunoglobulin Fc derived from animals such as cow, goats, pigs, mice, rabbits, hamsters, rats, and guinea pigs. In addition, the immunoglobulin Fc region may be derived from IgG, IgA, IgD, IgE, IgM, or a combination or hybrid thereof. Preferably, the immunoglobulin Fc is derived from IgG or IgM which are most abundant in human blood, and most preferably, it is derived from IgG which is known to improve half-life of ligand-binding protein. Also, the immunoglobulin Fc region may be a dimer or multimer of single-chain immunoglobulins having domains of same origin. Immunoglobulin Fc may be generated by treating a native IgG with a certain protease, or by transformed cells using a genetic recombination technique. Preferably, the immunoglobulin Fc is a recombinant human immunoglobulin Fc produced in E. coli.

Meanwhile, IgG may be divided into the IgG1, IgG2, IgG3 and IgG4 subclasses, and in the present invention a combination or hybrid thereof may be used. Preferred are the IgG2 and IgG4 subclasses, and most preferred is the Fc region of IgG4 which rarely has the effector function such as complement dependent cytotoxicity (CDC). That is, the most preferred immunoglobulin Fc region as a drug carrier of the present invention is a human IgG4-derived aglycosylated Fc region. The human-derived Fc region is more preferable than a non-human derived Fc region, which may act as an antigen in the human body and cause undesirable immune responses such as producing a new antibody.

The long-acting insulinotropic peptide conjugate used in the present invention is prepared by combining the synthesized insulinotropic peptide and an immunoglobulin Fc region. The method for combining the two may be cross-linking an insulinotropic peptide and an immunoglobulin Fc region via a non-peptidyl polymer or the production of a fusion protein in which insulinotropic peptide and an immunoglobulin Fc region are linked by genetic recombination.

The non-peptidyl polymer used for the cross-linking may be selected from the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers such as PLA (poly (lactic acid) and PLGA (poly (lactic-glycolic acid), lipid polymers, chitins, hyaluronic acid or a combination thereof. Preferably, polyethylene glycol may be used but is not limited thereto. Their derivatives well known in the art and derivatives which can be readily prepared using a method known in the art are also within the scope of the present invention.

For preparing a long-acting insulinotropic peptide conjugate used in the present invention, the entire specifications of Korean Patent Registration No. 10-0725315, Korean Patent Publication No. 10-2009-0008151 (corresponding to WO2009-011544 A2), and Korean Patent Registration No. 10-1058290 (corresponding to WO2008-082274 A1) are incorporated herein as references of the present invention. Those skilled in the art can produce the long-acting insulinotropic peptide conjugate of the present invention by referring to these references.

The liquid formulation of long-acting insulinotropic peptide conjugate of the present invention comprises a long-acting insulinotropic peptide conjugate in a therapeutically effective amount. In general, the therapeutically effective amount of insulinotropic peptide, especially exendin-4 (Byetta), refers to 250 mcg in a pen-injector. The concentration of long-acting insulinotropic peptide conjugate in the formulation of the present invention ranges from about 0.1 mg/mL to about 200 mg/mL, from about 0.5 mg/mL to 150 mg/mL, from about 4.0 mg/mL to about 50 mg/mL, or from about 4.0 mg/mL to about 20 mg/mL.

As used herein, the term "about" refers to a range including ±0.5, ±0.4, ±0.3, ±0.2, ±0.1, ±0.05, ±0.01, ±0.005, ±0.001, etc., and the term "about" includes any numerical value that is equivalent or in the range being similar to the numerical value following the term, but is not limited to.

The insulinotropic peptide may preferably be a long-acting CA exendin-4 conjugate. The liquid formulation of long-acting insulinotropic peptide conjugate of the present invention can stably store the conjugate without precipitation, not only when the insulinotropic peptide conjugate is present at low concentration, but also when it is present at high concentration. Therefore, the present formulation can stably provide the insulinotropic peptide at high concentration into the body.

As used herein, the term "stabilizer" refers to a substance that allows stable storing of the long-acting insulinotropic peptide conjugate. The term "stabilization" refers to the state wherein loss of an active ingredient is less than a certain amount, typically less than 10% during a certain period and under specific storage conditions. A formulation is regarded as a stable formulation when the residual purity of long-acting insulinotropic peptide conjugate therein is 90% or more, and more preferably 92 to 95% after being stored at 5±3° C. for 2 years, at 25±2° C. for 6 months, or at 40±2° C. for 1 to 2 weeks. As for the proteins like long-acting insulinotropic peptide conjugates, the storage stability thereof is important for providing an accurate dosage as well as for suppressing the potential formation of antigenic substances against the long-acting insulinotropic peptide conjugate. During storage, 10% loss of long-acting insulinotropic peptide conjugate is acceptable for a substantial administration unless it causes the formation of aggregates or fragments in the composition leading to the formation of antigenic compounds.

The stabilizer of the present invention preferably comprises a buffer, a sugar alcohol, and a non-ionic surfactant, and more preferably comprises methionine in addition, for stabilizing the long-acting insulinotropic peptide conjugate.

The buffer works to maintain the pH of solution to prevent a sharp pH change in the liquid formulation for stabilizing long-acting insulinotropic peptide conjugate. The buffer may include an alkaline salt (sodium or potassium phosphate or hydrogen or dihydrogen salts thereof), sodium citrate/citric acid, sodium acetate/acetic acid, histidine/histidine hydrochloride, any other pharmaceutically acceptable pH buffer known in the art, and a combination thereof. The preferred example of such buffer includes a citrate buffer, an acetate buffer, and a histidine buffer. Further, in the formulation, the citrate may be present in the form of citric acid monohydrate.

The concentration of buffering agent in the formulation may be about 5 mM to about 100 mM, specifically about 10 mM to about 100 mM, and more specifically about 10 mM to about 50 mM.

For example, the concentration of citrate in the formulation may be about 5 mM to about 100 mM, specifically about 10 mM to about 100 mM, and more specifically about 10 mM to about 50 mM. Further, the citric acid monohydrate may be present in the formulation in an amount of about 1 mg/mL to about 22 mg/mL, specifically about 2 mg/mL to about 22 mg/mL, and more specifically about 2 mg/mL to about 10 mg/mL.

The pH of buffer or formulation may be about 4.0 to about 7.0, specifically about 5.0 to about 7.0, more specifically about 5.2 to about 7.0, and even more specifically 5.2 to 6.0. Further, the pH of buffer or formulation may be about 5.4 to about 7.0, and specifically about 5.4 to about 6.0.

For preparation of the formulation, the pH of the formulation can be adjusted by using HCl and/or NaOH.

Sugar alcohol acts to increase the stability of the long-acting insulinotropic peptide conjugate. The concentration of the sugar alcohol used in the present invention may be about 1% (w/v) to about 20% (w/v) based on a total volume of solution, specifically, about 2% (w/v) to about 20% (w/v) based on a total volume of solution, and more specifically, about 2% (w/v) to about 10% (w/v) based on a total volume of solution, and even more specifically, about 3% (w/v) to about 10% (w/v) based on a total volume of solution. For example, the sugar alcohol may be present in the formulation in an amount of about 10 mg/mL to about 200 mg/mL, specifically about 20 mg/mL to about 200 mg/mL, more specifically about 20 mg/mL to about 100 mg/mL, and even more specifically, about 30 mg/mL to about 100 mg/mL, but is not limited thereto.

A sugar alcohol may be one or more selected from the group consisting of mannitol, sorbitol, and sucrose, but is not limited thereto.

The non-ionic surfactant can reduce the surface tension of the protein solution to prevent the absorption or aggregation of proteins onto a hydrophobic surface. Examples of the non-ionic surfactant useful in the present invention include polysorbates, poloxamers and combinations thereof, with preference for polysorbates. Among the non-ionic surfactants of polysorbates are polysorbate 20, polysorbate 40, polysorbate 60, and polysorbate 80. The most preferred non-ionic surfactant is polysorbate 20.

It is inappropriate to use a non-ionic surfactant at high concentration in liquid formulation, and this is due to the fact that non-ionic surfactant at high concentration induces interference effects when measuring protein concentration and determining protein stability through analytic methods such as UV-spectroscopy or isoelectric focusing, thereby causing difficulty in examining the protein stability accurately. Therefore, the liquid formulation of the present invention can comprise the non-ionic surfactant at a low concentration no more than 0.2% (w/v), specifically at about 0.1% (w/v) or less, more specifically at about 0.001% (w/v) to about 0.1% (w/v), and even more specifically, at about 0.001% (w/v) to about 0.05% (w/v). For example, the non-ionic surfactant may be present in the formulation in an amount of about 2 mg/mL or less, specifically about 1 mg/mL or less, more specifically about 0.01 mg/mL to about 1 mg/mL, and even more specifically, about 0.01 mg/mL to about 0.5 mg/mL.

The formulation according to the present invention may further comprise an isotonic agent.

An isotonic agent can act to maintain an appropriate osmotic pressure when the long-acting insulinotropic peptide conjugate in solution is administered into the body, and also can act to stabilize the long-acting insulinotropic peptide conjugate in solution. The osmotic pressure of formulation is adjusted to be isotonic with blood. These isotonic liquid formulations have osmotic pressure of about 300 mOsm/kg in general. A representative example of isotonic agent includes a sugar alcohol, a water-soluble inorganic salt, and an amino acid, and a preferred example is a water-soluble inorganic salt, i.e. sodium chloride. The concentration of sodium chloride as isotonic agent may be about 0 mM to about 150 mM, and it can be adjusted depending on the type and amount of components included in the formulation such that the liquid formulation including the entire mixture becomes isotonic.

According to one example of the present invention, it was demonstrated that when sodium chloride was added as isotonic agent in the presence of buffer, sugar alcohol, and non-ionic surfactant, the storage stability of long-acting insulinotropic peptide conjugate at low concentration was significantly increased. This indicates that use of sodium chloride as isotonic agent simultaneously with buffer, sugar alcohol, and non-ionic surfactant induces synergic effects, thereby allowing the long-acting insulinotropic peptide conjugate to have a high stability. However, as for a long-acting insulinotropic peptide conjugate at high concentration, when sodium chloride was excluded, the occurrence of precipitation was prevented and the solubility of protein was improved. These results suggest that when sodium chloride is used as an isotonic agent, the content thereof may be adjusted according to the concentration of long-acting insulinotropic peptide conjugate.

In addition, it was confirmed that a long-acting insulinotropic peptide conjugate at low concentration is most stable in a buffer at a pH of 5.2, whereas a long-acting insulinotropic peptide conjugate at high concentration is most stable in a buffer at a pH of 5.4 or 5.6. Thus, it was determined that the pH of buffer can be appropriately adjusted depending on the concentration of conjugate.

Methionine comprised in the stabilizer of the present invention suppresses the formation of impurities which may occur by oxidation of protein in solution, thereby stabilizing a target protein even further. For example, the concentration of methionine is about 0.005% (w/v) to about 0.1% (w/v) based on a total volume of solution, specifically about 0.01% (w/v) to about 0.1% (w/v). For example, the methionine may be present in the formulation in an amount of 0.05 mg/mL to 1 mg/mL, specifically, 0.1 mg/mL to 1 mg/mL.

It is preferred that the stabilizer of the present invention does not contain albumin. Since the human serum albumin available as a stabilizer of protein is produced from human serum, there is always the possibility that it may be contaminated with pathogenic viruses of human origin. Gelatin or bovine serum albumin may cause diseases or may be apt to induce an allergic response in some patients. Free of heterologous proteins such as serum albumins of human or animal origin or purified gelatin, the stabilizer of the present invention has no possibility of causing viral contamination.

In addition, the stabilizer of the present invention may further comprise sugars, polyalcohol, or amino acids. Preferable examples of sugars, which may be further added to increase the storage stability of the long-acting insulinotropic peptide conjugate, include monosaccharides such as mannose, glucose, fucose and xylose, and polysaccharides such as lactose, maltose, sucrose, raffinose and dextran. Preferred examples of polyalcohol include propylene glycol, low-molecular weight polyethylene glycol, glycerol, low-molecular weight polypropylene glycol, and a combination thereof.

The liquid formulation of the present invention may further comprise a preservative in addition to the above-described conjugate, buffer, sugar alcohol, and non-ionic surfactant, or additionally methionine, for the purpose of preventing microbial contamination in multiple-use formulation.

As used herein, "preservative" refers to a compound that is added to a pharmaceutical formulation to act as an antimicrobial. Example of preservative includes benzethonium, chlorohexidine, phenol, m-cresol, benzyl alcohol, methylparaben, propylparaben, chlorobutanol, o-cresol, p-cresol, chlorocresol, benzalconium chloride, phenylmercuric nitrate, thimerosal, and benzoic acid, but is not limited thereto. A single type of preservative may be used individually, or a random combination of two or more types of preservative may be used. Preferably, the liquid formulation of the present invention may comprise one or more of m-cresol, phenol, and benzyl alcohol as a preservative.

The liquid formulation of the present invention may comprise about 0.001% (w/v) to about 1% (w/v) preservative, and preferably about 0.001% (w/v) to about 0.5% (w/v) preservative, and more preferably about 0.001% (w/v) to about 0.25% (w/v) preservative.

In one example of the present invention, 0.22% (w/v) m-cresol was added as a preservative in the liquid formulation of the present invention, and the effect of cresol on the stability of insulinotropic peptide conjugate was evaluated. As a result, it was confirmed that the conjugate remained stable in the formulation added with preservative, without precipitation. Therefore, the liquid formulation of insulinotropic peptide conjugate of the present invention, which comprises preservative in addition to the stabilizer, may be used for multiple administrations.

The liquid formulation of the present invention may further comprise other substances and materials known in the art selectively in addition to the above-described buffer, sugar alcohol, and non-ionic surfactant, or additionally methionine and preservative, as long as the effect of the present invention is not affected.

The albumin-free liquid formulation of long-acting insulinotropic peptide conjugate according to the present invention providing stability to the long-acting insulinotropic peptide conjugate does not have a risk of viral contamination, while providing an excellent storage stability with a simple formulation, and thus the present formulation can be provided more cost-effectively compared to other stabilizer or free-dried formulation.

Also, since the liquid formulation of the present invention comprises the long-acting insulinotropic peptide conjugate which has an enhanced duration of physiological activity compared to a wild-type, it can be used as an effective drug formulation by retaining the protein activity in the body for a longer period compared to the conventional insulinotropic peptide formulation. Also, the present liquid formulation provides an excellent stability for storing a long-acting insulinotropic peptide conjugate at high concentration as well as at low concentration.

As another aspect, the present invention provides a method for preparing the liquid formulation of the present invention.

A stable liquid formulation of long-acting insulinotropic peptide conjugate can be prepared through providing long-acting insulinotropic peptide conjugate, and mixing the provided long-acting insulinotropic peptide conjugate with a stabilizer comprising a buffer, sugar alcohol, and non-ionic surfactant, and optionally, methionine. Also, for multiple uses, a stable liquid formulation of long-acting insulinotropic peptide conjugate may be generated by further mixing a preservative in addition to the stabilizers.

Hereinafter, the present invention will be described in more detail with reference to Examples. However, these Examples are for illustrative purposes only, and the invention is not intended to be limited by these Examples.

an isotonic agent in the formulation comprising a buffer, a sugar alcohol, and a non-ionic surfactant as a stabilizer; and in the formulation comprising a buffer, a sugar alcohol, a non-ionic surfactant, and methionine as a stabilizer. For this purpose, the long-acting insulinotropic peptide conjugate was stored at 25° C. and 40° C. for 0 to 4 weeks in the following compositions of Table 1, and then the stability of the conjugate was analyzed by reverse phase-high performance liquid chromatography (RP-HPLC) and size exclusion-high performance liquid chromatography (SE-HPLC). Citrate buffer was used as a buffer, mannitol was used as a sugar alcohol, and polysorbate 20 was used as a non-ionic surfactant. In Tables 2 and 3, RP-HPLC (%) and SE-HPLC (%) represent the value of "area %/start area %" showing the residual purity of the long-acting insulinotropic peptide conjugate compared to the initial purity. Table 2 shows the residual purity of long-acting insulinotropic peptide conjugate after being stored at 25° C., and Table 3 shows the residual purity of long-acting insulinotropic peptide conjugate after being stored at 40° C.

TABLE 1

| No. | Concentration | Buffer | Salt | Sugar alcohol | surfactant |
|---|---|---|---|---|---|
| 1 | 0.2 mg/mL | 20 mM Na-Citrate (pH 5.2) | 150 mM NaCl | 5% Mannitol | 0.005% Polysorbate 20 |
| 2 | 0.2 mg/mL | 20 mM Na-Citrate (pH 5.2) | — | 5% Mannitol | 0.005% Polysorbate 20 |
| 3 | 0.2 mg/mL | 20 mM Na-Citrate (pH 5.2) | — | 5% Mannitol/ 0.1 mg/mL Methionine | 0.005% Polysorbate 20 |
| 4 | 0.2 mg/mL | 20 mM Na-Citrate (pH 5.2) | 150 mM NaCl | 5% Mannitol/ 0.1 mg/mL Methionine | 0.005% Polysorbate 20 |

TABLE 2

| | RP-HPLC (%) | | | | SE-HPLC (%) | | | |
|---|---|---|---|---|---|---|---|---|
| No. | 0 week | 1 week | 2 weeks | 4 weeks | 0 week | 1 week | 2 weeks | 4 weeks |
| 1 | 100 | 99.3 | 99.2 | 97.1 | 100 | 99.8 | 100.1 | 100.2 |
| 2 | 100 | 99.1 | 99.1 | 96.9 | 100 | 99.8 | 100.1 | 100.1 |
| 3 | 100 | 99.8 | 99.5 | 97.9 | 100 | 99.8 | 100.0 | 100.1 |
| 4 | 100 | 99.5 | 99.8 | 98.4 | 100 | 99.9 | 100.2 | 100.2 |

TABLE 3

| | RP-HPLC (%) | | | | SE-HPLC (%) | | | |
|---|---|---|---|---|---|---|---|---|
| No. | 0 week | 1 week | 2 weeks | 4 weeks | 0 week | 1 week | 2 weeks | 4 weeks |
| 1 | 100 | 96.6 | 93.7 | 88.0 | 100 | 100.0 | 98.8 | 97.2 |
| 2 | 100 | precipitation | precipitation | Precipitation | 100 | precipitation | precipitation | precipitation |
| 3 | 100 | 98.1 | precipitation | Precipitation | 100 | 99.9 | precipitation | precipitation |
| 4 | 100 | 96.9 | 95.2 | 90.6 | 100 | 100.0 | 99.0 | 97.2 |

Example 1

Evaluation of the Stability of Long-Acting Insulinotropic Peptide Conjugate in the Presence or Absence of Isotonic Agent Such as Salt The stability of long-acting insulinotropic peptide conjugate (15.41 μg/mL CA exendin-4, Nominal Conc.) was evaluated in the presence or absence of sodium chloride as Based on the comparison between Test groups #1 and #2, and between #3 and #4 in Tables 2 and 3, it is evident that when the liquid formulation of long-acting insulinotropic peptide conjugate was stored at 25° C. and 40° C., especially at 40° C. for 4 weeks, and in the presence of NaCl as isotonic agent, particularly 150 mM NaCl, the stability of the long-acting insulinotropic peptide conjugate was maintained remarkably high (Tables 2 and 3).

Example 2

Evaluation of the Stability of Long-Acting Insulinotropic Peptide Conjugate at Various pH of Buffer While the pH range of the general liquefied protein drug is in 5 to 7, the pH of liquid formulation of exendin-4 (Byetta), an insulinotropic peptide drug, is 4.5, which is lower than the general pH range. Therefore, in this Example, the effect of pH of buffer on stability of conjugate was examined for a long-acting insulinotropic peptide conjugate comprising insulinotropic peptide and immunoglobulin Fc protein, preferably long-acting imidazoacetyl (CA) exendin-4 conjugate.

Citrate buffer was used as a buffer, mannitol was used as a sugar alcohol, sodium chloride was used as an isotonic agent, and polysorbate 80 was used as a non-ionic surfactant. The following compositions shown in Table 4 were used as a stabilizer for the long-acting insulinotropic peptide conjugate. Then the compositions of long-acting insulinotropic peptide conjugate were stored at 25±2° C. for 4 weeks and the stability thereof was analyzed by size exclusion chromatography (SE-HPLC) and reverse phase chromatography (RP-HPLC). RP-HPLC (%) and SE-HPLC (%) in Table 5 represent "area %/start area %" demonstrating the residual purity of the long-acting insulinotropic peptide conjugate in comparison with the initial purity.

TABLE 4

| Formulation No. | Concentration (mcg/mL) | Buffer | Surfactant | Sugar alcohol | Isotonic agent |
|---|---|---|---|---|---|
| 1 | 197.6 | 20 mM Na-Citrate (pH 5.2) | 0.005% Polysorbate 80 | 5% Mannitol | 150 mM NaCl |
| 2 | 197.6 | 20 mM Na-Citrate (pH 5.5) | 0.005% Polysorbate 80 | 5% Mannitol | 150 mM NaCl |
| 3 | 197.6 | 20 mM Na-Citrate (pH 6.0) | 0.005% Polysorbate 80 | 5% Mannitol | 150 mM NaCl |

TABLE 5

| Formulation No. | pH | RP-HPLC (Area %/Start Area %) % | | | | SE-HPLC (Area %/Start Area %) % | | | |
|---|---|---|---|---|---|---|---|---|---|
| | | 0 W | 1 W | 2 W | 4 W | 0 W | 1 W | 2 W | 4 W |
| 1 | 5.2 | 100.0 | 99.1 | 98.6 | 97.5 | 100.0 | 100.0 | 100.5 | 100.5 |
| 2 | 5.5 | 100.0 | 99.8 | 97.7 | 95.0 | 100.0 | 99.6 | 100.8 | 100.7 |
| 3 | 6.0 | 100.0 | 98.3 | 98.1 | 94.8 | 100.0 | 99.6 | 100.7 | 100.7 |

As shown above, when the pH was 5.2 in the above liquid formulation, the long-acting insulinotropic peptide conjugate was most stable (Table 5).

Example 3

Evaluation of the Stability of Long-Acting Insulinotropic Peptide Conjugate Depending on the Type and Concentration of Non-Ionic Surfactant The stability of long-acting insulinotropic peptide conjugate was examined using different types and concentrations of polysorbate which is a non-ionic surfactant in the stabilizer of the present invention.

The non-ionic surfactants, i.e., polysorbate 80 and polysorbate 20, were examined at both concentrations of 0.005% and 0.01%. The composition of stabilizer comprises a buffer, a sugar alcohol, and an isotonic agent as well as surfactant, as used in the above example for providing stability to the long-acting insulinotropic peptide conjugate. Citrate buffer at a pH of 5.2, which showed high stability in Example 2, was used as a buffer, mannitol was used as a sugar alcohol, and sodium chloride was used as an isotonic agent.

The following compositions shown in Table 6 were used as a stabilizer for long-acting insulinotropic peptide conjugate, preferably for long-acting CA exendin-4 conjugate. Then the compositions were stored at 25±2° C. for 8 weeks and the stability thereof was analyzed by RP-HPLC and SE-HPLC. RP-HPLC (%) and SE-HPLC (%) in Table 7 represent the residual purity of the long-acting insulinotropic peptide conjugate as compared to the initial purity.

TABLE 6

| Formulation No. | Concentration (mcg/mL) | Buffer | Surfactant | Sugar alcohol | Isotonic agent |
|---|---|---|---|---|---|
| 1 | 197.6 | 20 mM Na-Citrate (pH 5.2) | 0.005% Polysorbate 80 | 5% Mannitol | 150 mM NaCl |
| 2 | 197.6 | 20 mM Na-Citrate (pH 5.2) | 0.01% Polysorbate 80 | 5% Mannitol | 150 mM NaCl |
| 3 | 197.6 | 20 mM Na-Citrate (pH 5.2) | 0.005% Polysorbate 20 | 5% Mannitol | 150 mM NaCl |
| 4 | 197.6 | 20 mM Na-Citrate (pH 5.2) | 0.01% Polysorbate 20 | 5% Mannitol | 150 mM NaCl |

TABLE 7

| Formulation No. | Surfactant | RP-HPLC (Area %/Start Area %) % | | | | SE-HPLC (Area %/Start Area %) % | | | |
|---|---|---|---|---|---|---|---|---|---|
| | | 0 W | 2 W | 4 W | 8 W | 0 W | 2 W | 4 W | 8 W |
| 1 | 0.005% Polysorbate 80 | 100.0 | 97.5 | 94.1 | 90.9 | 100.0 | 100.0 | 100.0 | 99.9 |
| 2 | 0.01% Polysorbate 80 | 100.0 | 98.3 | 95.2 | 92.6 | 100.0 | 99.9 | 99.9 | 99.8 |

TABLE 7-continued

| Formulation | | RP-HPLC (Area %/Start Area %) % | | | | SE-HPLC (Area %/Start Area %) % | | | |
|---|---|---|---|---|---|---|---|---|---|
| No. | Surfactant | 0 W | 2 W | 4 W | 8 W | 0 W | 2 W | 4 W | 8 W |
| 3 | 0.005% Polysorbate 20 | 100.0 | 98.9 | 97.5 | 93.8 | 100.0 | 100.0 | 99.9 | 99.9 |
| 4 | 0.01% Polysorbate 20 | 100.0 | 98.69 | 97.0 | 92.2 | 100.0 | 100.0 | 100.0 | 99.1 |

As shown above, based on the SE-HPLC analysis results, the stability of the long-acting insulinotropic peptide conjugate was almost the same even when different types and concentrations of polysorbates were used. However, based on the RP-HPLC analysis results, it was observed that when polysorbate 20 was used, the stability of peptide conjugate was similar to or higher than when the same concentration of polysorbate 80 was used. Also, the stability of long-acting insulinotropic peptide conjugate was higher in the liquid formulation comprising 0.005% polysorbate 20, compared to the one comprising 0.01% polysorbate 20 (Table 7).

Example 4

Comparison of Stability Between the Finally Selected Liquid Formulation of Long-Acting Insulinotropic Peptide Conjugate and the Commercially Available Liquid Formulation of Peptide or Protein Drug Comprising the Same In the present example, the stability of the formulation that was selected through stability tests in Examples 1 to 3 was evaluated. The finally selected formulation of long-acting insulinotropic peptide conjugate comprises citrate buffer at a pH of 5.2, sodium chloride, mannitol, and polysorbate 20. For this purpose, the stability of drug formulations was compared between the liquid formulations which are generated by applying the long-acting insulinotropic peptide conjugate to a liquid formulation of commercially available insulinotropic peptide drug, exendin-4 (Byetta); and to a liquid formulation of immunoglobulin fusion protein drug, Etanercept (TNFR-Fc fusion protein, ENBREL).

Using the following compositions shown in Table 8, the following formulations were prepared: a liquid formulation of long-acting insulinotropic peptide conjugate, more preferably long-acting CA exendin-4 conjugate (Liquid Formulation #1); a liquid formulation prepared by applying the long-acting insulinotropic peptide conjugate to the stabilizer composition of the liquid formulation of insulinotropic peptide drug, exendin-4 (Byetta) (Liquid Formulation #2); and a liquid formulation prepared by applying the long-acting insulinotropic peptide conjugate to the stabilizer composition of the liquid formulation of immunoglobulin fusion protein drug, Etanercept (TNFR-Fc fusion protein, ENBREL) (Liquid Formulation #3). As a control group, a liquid formulation was prepared by applying the long-acting insulinotropic peptide conjugate to a stabilizer composition comprising PBS only (Liquid Formulation #4). Subsequently, the formulations were stored at 25±2° C. for 8 weeks, and the stability thereof was analyzed by RP-HPLC and SE-HPLC. RP-HPLC (%) and SE-HPLC (%) in Table 9 show the residual purity of the long-acting insulinotropic peptide conjugate as compared to the initial purity.

TABLE 8

| Formulation No. | Concentration (mcg/mL) | Buffer | Surfactant | Sugar alcohol and other | Isotonic agent |
|---|---|---|---|---|---|
| 1 | 197.6 | 20 mM Na-Citrate (pH 5.2) | 0.005% Polysorbate 20 | 5% Mannitol | 150 mM NaCl |
| 2 | 197.6 | 20 mM Na-Acetate (pH 4.5) | — | 5% Mannitol | — |
| 3 | 197.6 | 20 mM Na-Phosphate (pH 6.3) | — | 1% Sucrose 25 mM L-Arginine | 100 mM NaCl |
| 4 | 197.6 | PBS | — | — | — |

TABLE 9

| | RP-HPLC (Area %/Start Area %) % | | | | SE-HPLC (Area %/Start Area %) % | | | |
|---|---|---|---|---|---|---|---|---|
| No. | 0 W | 2 W | 4 W | 8 W | 0 W | 2 W | 4 W | 8 W |
| 1 | 100.0 | 98.9 | 97.5 | 93.8 | 100.0 | 100.0 | 100.0 | 99.9 |
| 2 | 100.0 | 98.4 | 96.6 | 90.9 | 100.0 | 100.1 | 99.9 | 99.2 |
| 3 | 100.0 | 95.4 | 89.1 | N/A | 100.0 | 100.0 | 100.0 | 99.7 |
| 4 | 100.0 | 92.7 | 84.1 | 69.2 | 100.0 | 100.0 | 99.9 | 99.6 |

As a result of stability test, it was observed that the liquid formulation of long-acting insulinotropic peptide conjugate of the present invention showed higher stability than the liquid formulations prepared by applying the long-acting insulinotropic peptide conjugate to the liquid formulations of a commercially available insulinotropic peptide drug, exendin-4 (Byetta), and an immunoglobulin fusion protein drug, Etanercept (TNFR-Fc usion protein, ENBREL), as shown in FIG. 1 and Table 9.

Example 5

Evaluation of the Stability of Long-Acting Insulinotropic Peptide Conjugate Depending on the Addition of Methionine In order to determine the effect of methionine on the stability of the conjugate, the liquid formulation was prepared by adding methionine for preventing oxidation, to the composition comprising citrate buffer at a pH of 5.2, sodium chloride, mannitol, and polysorbate 20, which were selected in the above Examples. The formulations were stored at 25±2° C. for 4 weeks and at 40±2° C. for 4 weeks, and then the stability thereof were analyzed.

The liquid formulation of long-acting insulinotropic peptide conjugate, more preferably the long-acting CA exendin-4 conjugate was prepared in the following compositions shown in Table 10 and the stability thereof was analyzed. RP-HPLC (%) and SE-HPLC (%) in Tables 11 to 14 represent the proportions of long-acting insulinotropic peptide conjugate and impurities at each time point. Table 11 shows the results of accelerated stability test by RP-HPLC (25±2° C.) and Table 12 shows the results of accelerated stability test by SE-HPLC (25±2° C.). Table 13 shows the results of instability severity test by RP-HPLC (40±2° C.) and Table 14 shows the results of instability severity test by SE-HPLC (40±2° C.). Impurity #3 represents the oxidized form of long-acting insulinotropic peptide conjugate. However, since SE-HPLC separates the sample by molecular weight and the difference in molecular weight between oxidized form and non-oxidized form is minor, it was hard to isolate the oxidized form of long-acting insulinotropic peptide conjugate through SE-HPLC.

TABLE 10

| No. | Concentration (mcg/mL) | Buffer | Surfactant | Sugar alcohol & methionine | Isotonic agent |
|---|---|---|---|---|---|
| 1 | 200 | 20 mM Na-Citrate (pH 5.2) | 0.005% Polysorbate 20 | 5% Mannitol | 150 mM NaCl |
| 2 | 200 | 20 mM Na-Citrate (pH 5.2) | 0.005% Polysorbate 20 | 5% Mannitol 0.01% Methionine | 150 mM NaCl |

TABLE 11

| Formulation No. | Storage duration | Proportion of conjugate and impurity (Area %) | | | | | | | |
|---|---|---|---|---|---|---|---|---|---|
| | | #1 | #2 | #3 | Conjugate | #4 | #5 | #6 | Others |
| 1 | 0 week | 0.1 | 0.1 | 0.8 | 93.5 | 3.2 | 1.7 | 0.4 | 0.1 |
| | 1 week | 0.1 | 0.2 | 1.0 | 92.8 | 3.8 | 1.8 | 0.3 | <0.1 |
| | 2 weeks | 0.2 | 0.2 | 1.4 | 92.7 | 3.2 | 2.0 | 0.3 | <0.1 |
| | 4 weeks | 0.1 | 0.3 | 1.8 | 90.8 | 4.6 | 1.7 | 0.3 | 0.6 |
| 2 | 0 week | 0.1 | 0.2 | 0.7 | 93.7 | 3.5 | 1.4 | 0.4 | <0.1 |
| | 1 week | 0.1 | 0.2 | 0.7 | 93.2 | 3.8 | 1.6 | 0.3 | <0.1 |
| | 2 weeks | 0.1 | 0.2 | 0.8 | 93.5 | 3.2 | 1.8 | 0.3 | <0.1 |
| | 4 weeks | 0.1 | 0.3 | 0.6 | 92.2 | 4.3 | 2.0 | 0.4 | 0.2 |

TABLE 12

| Formulation No. | Storage Duration | Proporation of conjugate and impurity (Area %) | | | | | | |
|---|---|---|---|---|---|---|---|---|
| | | #1 | #2 | #3 | Conjugate | #4 | #5 | Others |
| 1 | 0 week | 0.2 | 0.3 | 0.0 | 99.5 | 0.0 | 0.0 | 0.0 |
| | 1 week | 0.2 | 0.5 | 0.0 | 99.3 | 0.0 | 0.0 | 0.0 |
| | 2 weeks | 0.2 | 0.2 | 0.0 | 99.6 | 0.0 | 0.0 | 0.0 |
| | 4 weeks | 0.1 | 0.2 | 0.0 | 99.7 | 0.0 | 0.0 | 0.0 |
| 2 | 0 week | 0.3 | 0.2 | 0.0 | 99.5 | 0.0 | 0.0 | 0.0 |
| | 1 week | 0.3 | 0.3 | 0.0 | 99.4 | 0.0 | 0.0 | 0.0 |
| | 2 weeks | 0.2 | 0.1 | 0.0 | 99.7 | 0.0 | 0.0 | 0.0 |
| | 4 weeks | 0.2 | 0.1 | 0.0 | 99.7 | 0.0 | 0.0 | 0.0 |

TABLE 13

| Formulation No. | Storage Duration | Proportion of conjugate and impurity (Area %) | | | | | | | |
|---|---|---|---|---|---|---|---|---|---|
| | | #1 | #2 | #3 | Conjugate | #4 | #5 | #6 | Others |
| 1 | 0 week | 0.1 | 0.1 | 0.8 | 93.5 | 3.2 | 1.7 | 0.4 | 0.1 |
| | 1 week | 0.2 | 0.3 | 1.5 | 90.3 | 5.0 | 2.4 | 0.3 | <0.1 |
| | 2 weeks | 0.1 | 0.5 | 2.1 | 87.6 | 6.2 | 3.2 | 0.3 | <0.1 |
| | 4 weeks | 0.1 | 1.1 | 3.7 | 82.3 | 8.6 | 3.8 | 0.3 | 0.2 |
| 2 | 0 week | 0.1 | 0.2 | 0.7 | 93.7 | 3.5 | 1.4 | 0.4 | <0.1 |
| | 1 week | 0.1 | 0.4 | 0.7 | 90.8 | 4.9 | 2.8 | 0.3 | 0.1 |
| | 2 weeks | 0.1 | 0.5 | 0.7 | 89.2 | 5.9 | 3.2 | 0.3 | 0.0 |
| | 4 weeks | 0.1 | 1.0 | 0.8 | 84.9 | 8.5 | 3.9 | 0.3 | 0.5 |

TABLE 14

| Formulation No. | Storage Duration | Proportion of conjugate and impurity (Area %) | | | | | | |
|---|---|---|---|---|---|---|---|---|
| | | #1 | #2 | #3 | Conjugate | #4 | #5 | Others |
| 1 | 0week | 0.2 | 0.3 | 0.0 | 99.5 | 0.0 | 0.0 | 0.0 |
| | 1week | 0.2 | 0.3 | 0.0 | 99.5 | 0.0 | 0.0 | 0.0 |
| | 2weeks | 0.2 | 0.0 | 0.0 | 98.3 | 1.3 | 0.3 | 0.0 |
| | 4weeks | 0.1 | 0.0 | 0.0 | 96.7 | 2.7 | 0.4 | 0.0 |
| 2 | 0week | 0.3 | 0.2 | 0.0 | 99.5 | 0.0 | 0.0 | 0.0 |
| | 1week | 0.2 | 0.3 | 0.0 | 99.5 | 0.0 | 0.0 | 0.0 |
| | 2weeks | 0.1 | 0.0 | 0.0 | 98.5 | 1.1 | 0.3 | 0.0 |
| | 4weeks | 0.1 | 0.0 | 0.0 | 96.7 | 2.3 | 0.5 | 0.0 |

As results of the accelerated stability test and instability severity test and as shown in FIG. 2, it was observed that the proportion of oxidized long-acting insulinotropic peptide conjugate (Impurity #3 in RP-HPLC analysis) was increased in the liquid formulation without methionine, but was not increased in the liquid formulation comprising 0.01% methionine (FIG. 2). Therefore, it was confirmed that the liquid formulation containing methionine can provide stability to the long-acting insulinotropic peptide conjugate more effectively.

Example 6

Evaluation of the Long-term Storage Stability of the Finally selected Liquid Formulation of Long-Acting Insulinotropic Peptide Conjugate In the present example, the liquid formulation that was finally selected by the above examples was evaluated for the long-term storage stability and accelerated stability. The finally selected liquid formulation comprises citrate buffer at a pH of 5.2, sodium chloride, mannitol, polysorbate 20, and methionine. For this purpose, the formulations were stored at 5±3° C. for 6 months and at 25±2° C. for 6 months and the stability thereof were analyzed. The results are shown in Tables 15 and 16, and RP-HPLC (%), SE-HPLC (%), protein content (%), and specific activity test (%) represent the residual purity of the conjugate compared to the initial purity. Table 15 shows the results of testing long-term storage stability of formulation after storing the same at 5±3° C., and Table 16 shows the results of accelerated stability test after storing the same at 25±2° C.

TABLE 15

Evaluation of long-term storage stability (stored at 5 ± 3° C.)

| Storage Duration | Color | pH | Confirmation test RP-HPLC | Western blot | SDS-PAGE | Purity test RP-HPLC (%) | SE-HPLC (%) | Endotoxin | Protein Content (%) | Specific activity (%) |
|---|---|---|---|---|---|---|---|---|---|---|
| Start | No color/ Transparent | 5.2 | Match | Acceptable | acceptable | 100.0 | 100.0 | acceptable | 100.0 | 100.0 |
| 1 month | No color/ Transparent | 5.2 | Match | acceptable | acceptable | 100.1 | 99.7 | acceptable | 105.8 | 114.3 |
| 3 months | No color/ Transparent | 5.2 | Match | acceptable | acceptable | 100.1 | 99.6 | acceptable | 100.0 | 115.7 |
| 6 months | No color/ Transparent | 5.2 | Match | acceptable | acceptable | 100.0 | 99.5 | acceptable | 100.0 | 97.0 |

TABLE 16

Accelerated stability Test (stored at 25 ± 2° C.)

| Storage Duration | Color | pH | Confirmation test RP-HPLC | Western blot | SDS-PAGE | Purity test RP-HPLC (%) | SE-HPLC (%) | Endotoxin | Protein Content (%) | Specific activity (%) |
|---|---|---|---|---|---|---|---|---|---|---|
| Start | No Color/ Transparent | 5.2 | match | acceptable | acceptable | 100.0 | 100.0 | acceptable | 100.0 | 100.0 |
| 1 month | No color/ Transparent | 5.2 | match | acceptable | acceptable | 99.6 | 99.4 | acceptable | 105.8 | 116.4 |
| 3 months | No color/ Transparent | 5.2 | match | acceptable | acceptable | 98.0 | 98.6 | acceptable | 103.8 | 95.8 |
| 6 months | No color/ Transparent | 5.2 | match | acceptable | acceptable | 95.4 | 97.7 | acceptable | 103.8 | 90.5 |

As a result of long-term storage stability test, the long-acting insulinotropic peptide conjugate was stable for more than 6 months in the liquid formulation of the present invention. Also, even when stored in the accelerated condition for 6 months, RP-HPLC analysis results showed that 95.4% or more of the peptide conjugate was remained intact in the formulation, thereby confirming that the present liquid formulation provides excellent storage stability to the long-acting insulinotropic peptide conjugate.

Example 7

Evaluation of the Stability of Long-Acting Insulinotropic Peptide Conjugate Depending on the Concentration of Protein The effect of high conjugate concentration was examined for the finally selected liquid formulation, comprising citrate buffer at a pH of 5.2, sodium chloride, mannitol, polysorbate 20, and methionine for preventing oxidation. For this purpose, the precipitation in the formulation was monitored with naked eyes at 40° C. and at various conjugate concentrations shown in Table 17. After 72 hours of monitoring, precipitation occurred in all of the present formulations at high concentration (4 mg/Ml or more). Also, as the concentration increased, the occurrence of precipitation was increased as well.

TABLE 17

| No. | Concentration | Buffer | Salt | Sugar alcohol and others | Surfactant |
|---|---|---|---|---|---|
| 1 | 0.52 mg/mL | 20 mM Na-Citrate (pH 5.2) | 150 mM NaCl | 5% Mannitol/ 0.1 mg/mL Methionine | 0.005% Polysorbate 20 |
| 2 | 4.0 mg/mL | 20 mM Na-Citrate (pH 5.2) | 150 mM NaCl | 5% Mannitol/ 0.1 mg/mL Methionine | 0.005% Polysorbate 20 |
| 3 | 5.0 mg/mL | 20 mM Na-Citrate (pH 5.2) | 150 mM NaCl | 5% Mannitol/ 0.1 mg/mL Methionine | 0.005% Polysorbate 20 |
| 4 | 8.0 mg/mL | 20 mM Na-Citrate (pH 5.2) | 150 mM NaCl | 5% Mannitol/ 0.1 mg/mL Methionine | 0.005% Polysorbate 20 |
| 5 | 10.0 mg/mL | 20 mM Na-Citrate (pH 5.2) | 150 mM NaCl | 5% Mannitol/ 0.1 mg/mL Methionine | 0.005% Polysorbate 20 |
| 6 | 13.0 mg/mL | 20 mM Na-Citrate (pH 5.2) | 150 mM NaCl | 5% Mannitol/ 0.1 mg/mL Methionine | 0.005% Polysorbate 20 |

Example 8

Evaluation of Stability of Long-Acting Insulinotropic Peptide Conjugate at High Concentration Depending on the Concentration of a Salt and a Sugar Alcohol, and the Presence of Methionine The effect of the concentration of NaCl and mannitol as a sugar alcohol on preventing the precipitation was examined for the finally selected liquid formulation of long-acting insulinotropic peptide conjugate at high concentration. The formulations were prepared in the following compositions shown in Table 18 and monitored for occurrence of precipitation with naked eyes at 40° C. for 48 hours. The duration of absence of precipitation shown in FIG. 3 demonstrates the time during which protein precipitation did not occur after storage.

TABLE 18

| No. | Concentration | Buffer | Salt | Sugar alcohol and others | Surfactant |
|---|---|---|---|---|---|
| 1 | 5.0 mg/mL | 20 mM Na-Citrate (pH 5.2) | 150 mM NaCl | 5% Mannitol/ 0.1 mg/mL Methionine | 0.005% Polysorbate 20 |
| 2 | 5.0 mg/mL | 20 mM Na-Citrate (pH 5.2) | 150 mM NaCl | 10% Mannitol/ 0.1 mg/mL Methionine | 0.005% Polysorbate 20 |
| 3 | 5.0 mg/mL | 20 mM Na-Citrate (pH 5.2) | 200 mM NaCl | 5% Mannitol/ 0.1 mg/mL Methionine | 0.005% Polysorbate 20 |
| 4 | 5.0 mg/mL | 20 mM Na-Citrate (pH 5.2) | 150 mM NaCl | 5% Mannitol/ | 0.005% Polysorbate 20 |

As shown in the above results, it was confirmed that the concentration of NaCl did not significantly affect the occurrence of precipitation and stability of the insulinotropic peptide conjugate at high concentration, based on the observation by naked eyes. However, when the concentration of mannitol as a sugar alcohol was increased from 5% to 10%, the precipitation could be suppressed significantly (FIG. 3). Also, when methionine was not added to the formulation, the precipitation could be suppressed as well.

Example 9

Evaluation of Stability of Long-Acting Insulinotropic Peptide Conjugate at High Concentration Depending on the Presence of a Salt and at Various pH Having 10% mannitol as selected by Example 8, the effect of pH was examined on the suppression of precipitation and the promotion of stability of long-acting insulinotropic conjugate at high concentration. Citrate buffer was used as a buffer, and polysorbate 20 was used as a non-ionic surfactant. According to Example 8, precipitation could be suppressed by exclusion of methionine from formulation. However methionine was still added to the formulation for the purpose of preventing oxidation of the protein. Furthermore, in order to confirm the synergic effect of NaCl and pH, 150 mM NaCl was added or excluded in the formulation. The long-acting insulinotropic peptide conjugate at high concentration was prepared in the following compositions shown in Table 19 and monitored for the occurrence of precipitation at 40° C. for 7 days. After 7 days of storing, the samples were analyzed by RP-HPLC and SE-HPLC.

The duration of the absence of precipitation shown in FIG. 4 indicates the time during which the protein precipitation did not occur after storage. RP-HPLC (%) of Table 20 and SE-HPLC (%) of Table 21 indicate the residual purity of the long-acting insulinotropic peptide conjugate compared to the initial purity.

TABLE 19

| No. | Concentration | Buffer | Salt | Sugar alcohol and others | Surfactant |
|---|---|---|---|---|---|
| 1 | 5.0 mg/mL | 20 mM Na-Citrate (pH 5.2) | — | 10% Mannitol/ 0.1 mg/mL Methionine | 0.005% Polysorbate 20 |
| 2 | 5.0 mg/mL | 20 mM Na-Citrate (pH 5.2) | 150 mM NaCl | 10% Mannitol/ 0.1 mg/mL Methionine | 0.005% Polysorbate 20 |
| 3 | 5.0 mg/mL | 20 mM Na-Citrate (pH 5.4) | — | 10% Mannitol/ 0.1 mg/mL Methionine | 0.005% Polysorbate 20 |
| 4 | 5.0 mg/mL | 20 mM Na-Citrate (pH 5.4) | 150 mM NaCl | 10% Mannitol/ 0.1 mg/mL Methionine | 0.005% Polysorbate 20 |
| 5 | 5.0 mg/mL | 20 mM Na-Citrate (pH 5.6) | — | 10% Mannitol/ 0.1 mg/mL Methionine | 0.005% Polysorbate 20 |
| 6 | 5.0 mg/mL | 20 mM Na-Citrate (pH 5.6) | 150 mM NaCl | 10% Mannitol/ 0.1 mg/mL Methionine | 0.005% Polysorbate 20 |

TABLE 20

| | RP-HPLC (Area %) | | | | | |
|---|---|---|---|---|---|---|
| No. | 0 D | 1 D | 2 D | 3 D | 4 D | 7 D |
| 1 | 98.5 | Precipitation | Precipitation | Precipitation | Precipitation | Precipitation |
| 2 | 98.4 | 98.0 | Precipitation | Precipitation | Precipitation | Precipitation |
| 3 | 98.4 | 97.9 | 97.7 | 97.6 | 97.3 | 96.8 |
| 4 | 98.3 | 98.0 | 97.7 | 97.6 | 97.2 | 96.3 |
| 5 | 98.2 | 97.8 | 97.8 | 97.5 | 97.4 | 96.5 |
| 6 | 98.3 | 98.1 | 97.9 | 97.5 | 97.2 | 96.5 |

TABLE 21

| | SE-HPLC (Area %) | | | | | |
|---|---|---|---|---|---|---|
| No. | 0 D | 1 D | 2 D | 3 D | 4 D | 7 D |
| 1 | 98.3 | Precipitation | Precipitation | Precipitation | Precipitation | Precipitation |
| 2 | 98.3 | 95.6 | Precipitation | Precipitation | Precipitation | Precipitation |
| 3 | 98.3 | 98.0 | 97.8 | 97.5 | 97.4 | 97.4 |
| 4 | 98.4 | 98.1 | 97.9 | 97.4 | 97.3 | 97.6 |
| 5 | 98.5 | 98.0 | 98.0 | 97.9 | 97.8 | 97.8 |
| 6 | 98.5 | 98.1 | 98.1 | 98.0 | 97.9 | 97.8 |

As shown above, the precipitation was suppressed better at the high pH of 5.4 and 5.6 than at the pH of 5.2. After 7 days of storing, precipitation was observed in all formulations. However, in the composition comprising 10% mannitol and 150 mM NaCl at a pH of 5.6 (Composition No. 6), the amount of impurity generated was smallest. At the pH of 5.4 and 5.6, the presence of NaCl did not have a significant effect on the stability of long-acting insulinotropic peptide conjugate at high concentration, except for the precipitation (Tables 20 and 21, and FIG. 4).

Example 10

Evaluation of Stability of Long-Acting Insulinotropic Peptide Conjugate at High Concentration Depending on the Concentration of Sugar Alcohol and at Various pH Based on the above Examples, the effect of concentration of sugar alcohol and pH on the stability of long-acting insulinotropic peptide conjugate at high concentration was examined. Citrate buffer was used as a buffer, and polysorbate 20 was used as a non-ionic surfactant. Also, methionine was added to the formulation for the purpose of preventing oxidation. In addition, based on the results observed in Example 9, NaCl was excluded in the formulation of long-acting insulinotropic peptide conjugate at high concentration. The long-acting insulinotropic peptide conjugate at high concentration was formulated in the following compositions as shown in Table 22 and stored at 40° C. for 5 days and moved to the temperature of 25° C. and stored for 4 more weeks. Every week, the stability of protein was analyzed by SE-HPLC, IE-HPLC, and RP-HPLC. SE-HPLC (%) of Table 23, IE-HPLC (%) of Table 24, and RP-HPLC (%) of Table 25 represent the residual purity of the long-acting insulinotropic peptide conjugate.

TABLE 22

| No. | Concentration | Buffer | Salt | Sugar alcohol and other | Surfactant |
|---|---|---|---|---|---|
| 1 | 10.0 mg/mL | 20 mM Na-Citrate (pH 5.6) | — | 10% Mannitol/ 0.1 mg/mL Methionine | 0.005% Polysorbate 20 |
| 2 | 10.0 mg/mL | 20 mM Na-Citrate (pH 5.2) | — | 10% Mannitol/ 0.1 mg/mL Methionine | 0.005% Polysorbate 20 |
| 3 | 10.0 mg/mL | 20 mM Na-Citrate (pH 6.0) | — | 10% Mannitol/ 0.1 mg/mL Methionine | 0.005% Polysorbate 20 |
| 4 | 10.0 mg/mL | 20 mM Na-Citrate (pH 6.0) | — | 2% Mannitol/ 0.1 mg/mL Methionine | 0.005% Polysorbate 20 |
| 5 | 10.0 mg/mL | 20 mM Na-Citrate (pH 6.4) | — | 2% Mannitol/ 0.1 mg/mL Methionine | 0.005% Polysorbate 20 |
| 6 | 10.0 mg/mL | 20 mM Na-Citrate (pH 6.0) | — | 5% Mannitol/ 0.1 mg/mL Methionine | 0.005% Polysorbate 20 |
| 7 | 10.0 mg/mL | 20 mM Na-Citrate (pH 6.4) | — | 5% Mannitol/ 0.1 mg/mL Methionine | 0.005% Polysorbate 20 |

TABLE 23

| | SE-HPLC (Area %) | | | | |
|---|---|---|---|---|---|
| No. | 0 W | 1 W | 2 W | 3 W | 4 W |
| 1 | 99.4 | 98.3 | 98.3 | 98.2 | 98.0 |
| 2 | 99.3 | 98.0 | 98.0 | 97.8 | 97.6 |
| 3 | 99.3 | 98.1 | 98.1 | 98.0 | 97.9 |
| 4 | 99.3 | 97.9 | 97.8 | 97.8 | 97.7 |
| 5 | 99.0 | 97.7 | 97.6 | 97.6 | 97.5 |
| 6 | 99.3 | 98.1 | 98.0 | 98.0 | 97.7 |
| 7 | 99.0 | 97.7 | 97.7 | 97.6 | 97.5 |

TABLE 24

| | IE-HPLC (Area %) | | | | |
|---|---|---|---|---|---|
| No. | 0 W | 1 W | 2 W | 3 W | 4 W |
| 1 | 95.6 | 81.7 | 78.2 | 75.7 | 65.3 |
| 2 | 95.7 | 73.8 | 69.0 | 64.6 | 53.3 |
| 3 | 95.7 | 81.7 | 79.9 | 77.1 | 69.1 |
| 4 | 95.6 | 80.3 | 78.0 | 75.3 | 66.4 |
| 5 | 95.6 | 72.7 | 70.8 | 68.3 | 60.2 |
| 6 | 95.7 | 80.6 | 77.1 | 72.3 | 61.6 |
| 7 | 95.7 | 74.1 | 70.2 | 69.8 | 62.7 |

TABLE 25

| | RP-HPLC (Area %) | | | | |
|---|---|---|---|---|---|
| No. | 0 W | 1 W | 2 W | 3 W | 4 W |
| 1 | 97.5 | 87.2 | 84.1 | 81.0 | 75.7 |
| 2 | 97.6 | 80.0 | 77.6 | 67.5 | 60.3 |
| 3 | 97.5 | 87.5 | 84.9 | 81.0 | 76.0 |
| 4 | 97.5 | 86.6 | 83.4 | 79.2 | 72.9 |
| 5 | 96.5 | 84.5 | 79.5 | 76.2 | 72.9 |
| 6 | 97.5 | 86.1 | 82.8 | 77.1 | 69.7 |
| 7 | 96.6 | 82.9 | 80.1 | 77.2 | 71.9 |

As shown above, when the pH was low, the stability was also reduced, compared to when the pH was high. The stability of the conjugate was highest at 10% mannitol, while 2% and 5% mannitol did not affect the stability of long-acting insulinotropic peptide conjugate at high concentration.

Example 11

Evaluation of the Stability of Long-Acting Insulinotropic Peptide Conjugate at High Concentration Depending on the Type and Concentration of Sugar Alcohol For developing an isotonic liquid formulation, the effect of the type and concentration of a sugar alcohol, which affects the osmotic pressure of the formulation most significantly, on the stability of insulinotropic peptide conjugate was examined under the same condition as in the above Examples. The type of sugar alcohol was changed to sucrose. Based on Formulation No. 1 of Example 10, 10% mannitol was replaced by 5% and 7% sucrose (Table 26). The formulations were stored at 25° C. for 4 weeks and the stability thereof was analyzed every week by SE-HPLC, IE-HPLC, and RP-HPLC. SE-HPLC (%) of Table 27, IE-HPLC (%) of Table 28, and RP-HPLC (%) of Table 29 represent the residual purity of the long-acting insulinotropic peptide conjugate.

TABLE 26

| No. | Concentration | Buffer | Salt | Sugar alcohol and others | Surfactant |
|---|---|---|---|---|---|
| 1 | 10.0 mg/mL | 20 mM Na-Citrate (pH 5.6) | — | 10% Mannitol/ 0.1 mg/mL Methionine | 0.005% Polysorbate 20 |
| 2 | 10.0 mg/mL | 20 mM Na-Citrate (pH 5.6) | — | 5% Sucrose/ 0.1 mg/mL Methionine | 0.005% Polysorbate 20 |
| 3 | 10.0 mg/mL | 20 mM Na-Citrate (pH 5.6) | — | 7% Sucrose/ 0.1 mg/mL Methionine | 0.005% Polysorbate 20 |

TABLE 27

| | SE-HPLC (Area %) | | | | |
|---|---|---|---|---|---|
| No. | 0 W | 1 W | 2 W | 3 W | 4 W |
| 1 | 99.4 | 98.3 | 98.3 | 98.2 | 98.0 |
| 2 | 99.5 | 98.4 | 98.3 | 98.2 | 98.0 |
| 3 | 99.5 | 98.5 | 98.4 | 98.3 | 98.1 |

TABLE 28

| | IE-HPLC (Area %) | | | | |
|---|---|---|---|---|---|
| No. | 0 W | 1 W | 2 W | 3 W | 4 W |
| 1 | 95.6 | 81.7 | 78.2 | 75.7 | 65.3 |
| 2 | 95.6 | 83.1 | 79.9 | 76.5 | 68.8 |
| 3 | 95.7 | 83.8 | 81.3 | 78.1 | 69.6 |

TABLE 29

| | RP-HPLC (Area %) | | | | |
|---|---|---|---|---|---|
| No. | 0 W | 1 W | 2 W | 3 W | 4 W |
| 1 | 97.5 | 87.2 | 84.1 | 81.0 | 75.7 |
| 2 | 97.5 | 88.5 | 85.0 | 80.9 | 75.3 |
| 3 | 97.5 | 90.1 | 85.8 | 82.5 | 76.0 |

As shown above, when sucrose was used instead of mannitol, the stability of the conjugate was maintained, and the stability of conjugate was increased slightly in 7% sucrose rather than in 5% sucrose, but there was no significant difference.

Example 12

Evaluation of Stability of Long-Acting Insulinotropic Peptide Conjugate at High Concentration Depending on the Type of Buffer, Adjustment of Osmotic Pressure, and Addition of Preservative In order to develop an isotonic liquid formulation, the concentration of sugar alcohol, which has the greatest effect on osmotic pressure, was adjusted and different types of buffers were tested for providing conjugate stability under the conditions of the above Examples. Also, under the same condition, 0.22% m-cresol was added as a preservative, and the effect thereof on the conjugate stability was tested as well. The long-acting insulinotropic peptide conjugate was formulated in the following compositions shown in Table 30 and stored at 25° C. for 2 weeks. Then every week, the stability of the samples were analyzed by SE-HPLC, IE-HPLC, and RP-HPLC. SE-HPLC (%) of Table 31, IE-HPLC (%) of Table 32, and RP-HPLC (%) of Table 33 represent the residual purity of the long-acting insulinotropic peptide conjugate.

TABLE 30

| No. | Concentration | Buffer | Salt | Sugar alcohol and others | Surfactant | Preservative |
|---|---|---|---|---|---|---|
| 1 | 10.0 mg/mL | 20 mM Na-Citrate (pH 5.6) | — | 10% Mannitol/ 0.1 mg/mL Methionine | 0.005% Polysorbate 20 | — |
| 2 | 10.0 mg/mL | 20 mM Na-Citrate (pH 5.6) | — | 5% Sucrose/ 0.1 mg/mL Methionine | 0.005% Polysorbate 20 | 0.22% m-cresol |
| 3 | 10.0 mg/mL | 20 mM Histidine-Cl (pH 5.6) | — | 7% Sucrose/ 0.1 mg/mL Methionine | 0.005% Polysorbate 20 | — |
| 4 | 10.0 mg/mL | 20 mM Histidine-Cl (pH 5.6) | — | 10% Mannitol/ 0.1 mg/mL Methionine | 0.005% Polysorbate 20 | 0.22% m-cresol |
| 5 | 10.0 mg/mL | 20 mM Na-Acetate (pH 5.6) | — | 5% Sucrose/ 0.1 mg/mL Methionine | 0.005% Polysorbate 20 | — |
| 6 | 10.0 mg/mL | 20 mM Na-Acetate (pH 5.6) | — | 7% Sucrose/ 0.1 mg/mL Methionine | 0.005% Polysorbate 20 | 0.22% m-cresol |

TABLE 31

| No. | SE-HPLC (Area %) | | |
|---|---|---|---|
| | 0 W | 1 W | 2 W |
| 1 | 99.4 | 98.9 | 97.0 |
| 2 | 99.3 | 99.2 | 98.6 |
| 3 | 99.2 | 98.9 | 98.4 |
| 4 | 99.1 | 98.8 | 98.0 |
| 5 | 99.3 | 99.1 | 98.7 |
| 6 | 99.2 | 99.1 | 98.4 |

TABLE 32

| No. | IE-HPLC (Area %) | | |
|---|---|---|---|
| | 0 W | 1 W | 2 W |
| 1 | 90.4 | 88.9 | 84.7 |
| 2 | 90.5 | 90.2 | 88.2 |
| 3 | 89.0 | 83.5 | 78.0 |
| 4 | 89.2 | 85.0 | 80.1 |
| 5 | 89.6 | 84.4 | 79.8 |
| 6 | 90.1 | 86.9 | 83.2 |

TABLE 33

| No. | RP-HPLC (Area %) | | |
|---|---|---|---|
| | 0 W | 1 W | 2 W |
| 1 | 93.2 | 91.3 | 90.1 |
| 2 | 93.2 | 91.9 | 90.1 |
| 3 | 91.8 | 88.2 | 80.3 |
| 4 | 92.4 | 88.6 | 84.4 |
| 5 | 91.5 | 87.6 | 83.8 |
| 6 | 92.2 | 89.4 | 86.0 |

As shown above, when different types of buffers were used, the peptide conjugate of each formulation was stable. Also, addition of m-cresol did not affect the peptide stability.

These results support that the composition of the liquid formulation of the present invention could maintain a high stability of the insulinotropic peptide conjugate at high concentration.

Example 13

Evaluation of the Stability of Long Acting Insulinotropic Peptide Conjugate According to pH of Buffer and Concentration of Non-Ionic Surfactant Based on existing exemplary embodiments, effects of pH of the buffer and concentrations of the non-ionic surfactant on the stability of the long acting insulinotropic peptide conjugate were examined.

Citrate buffer and polysorbate 20 were used as the buffer and the non-ionic surfactant, respectively. The following compositions shown in Table 34 were used, and the long-acting insulinotropic peptide conjugate was stored at 25° C. for 0 weeks to 4 weeks and was then analyzed using reverse phase (RP)-HPLC, ion exchange (IE)-HPLC, and size exclusion (SE)-HPLC. RP-HPLC (%), IE-HPLC (%), and SE-HPLC (%) of Table 35 represent (Area %/Start Area %), demonstrating the residual rate of the long-acting insulinotropic peptide conjugate in comparison with the initial value.

TABLE 34

| No. | Concentration | Buffer | Salt | Sugar alcohol and others | Surfactant |
|---|---|---|---|---|---|
| 1 | 10.0 mg/mL | 20 mM Na-Citrate (pH 3.5) | — | 10% Mannitol/ 0.1 mg/mL Methionine | 0.005% Polysorbate 20 |
| 2 | 10.0 mg/mL | 20 mM Na-Citrate (pH 4.5) | — | 10% Mannitol/ 0.1 mg/mL Methionine | 0.005% Polysorbate 20 |
| 3 | 10.0 mg/mL | 20 mM Na-Citrate (pH 5.2) | — | 10% Mannitol/ 0.1 mg/mL Methionine | 0.005% Polysorbate 20 |
| 4 | 10.0 mg/mL | 20 mM Na-Citrate (pH 5.6) | — | 10% Mannitol/ 0.1 mg/mL Methionine | 0.005% Polysorbate 20 |
| 5 | 10.0 mg/mL | 20 mM Na-Citrate (pH 7.0) | — | 10% Mannitol/ 0.1 mg/mL Methionine | 0.005% Polysorbate 20 |
| 6 | 10.0 mg/mL | 20 mM Na-Citrate (pH 7.5) | — | 10% Mannitol/ 0.1 mg/mL Methionine | 0.005% Polysorbate 20 |
| 7 | 10.0 mg/mL | 20 mM Na-Citrate (pH 8.5) | — | 10% Mannitol/ 0.1 mg/mL Methionine | 0.005% Polysorbate 20 |
| 8 | 10.0 mg/mL | 20 mM Na-Citrate (pH 5.6) | — | 10% Mannitol/ 0.1 mg/mL Methionine | 0.001% Polysorbate 20 |
| 9 | 10.0 mg/mL | 20 mM Na-Citrate (pH 5.6) | — | 10% Mannitol/ 0.1 mg/mL Methionine | 0.05% Polysorbate 20 |
| 10 | 10.0 mg/mL | 20 mM Na-Citrate (pH 5.6) | — | 10% Mannitol/ 0.1 mg/mL Methionine | 0.5% Polysorbate 20 |
| 11 | 10.0 mg/mL | 20 mM Na-Citrate (pH 5.6) | — | 10% Mannitol/ 0.1 mg/mL Methionine | 1.0% Polysorbate 20 |
| 12 | 10.0 mg/mL | 20 mM Na-Citrate (pH 5.6) | — | 10% Mannitol/ 0.1 mg/mL Methionine | 5.0% Polysorbate 20 |

TABLE 35

| No. | RP-HPLC (%) | | | IE-HPLC (%) | | | SE-HPLC (%) | | |
|---|---|---|---|---|---|---|---|---|---|
| | 0 weeks | 2 weeks | 4 weeks | 0 weeks | 2 weeks | 4 weeks | 0 weeks | 2 weeks | 4 weeks |
| 1 | 100 | 92.7 | precipitation | 100 | 81.0 | precipitation | 100 | 94.6 | precipitation |
| 2 | 100 | 93.2 | precipitation | 100 | 81.3 | precipitation | 100 | 94.5 | precipitation |
| 3 | 100 | 96.1 | 90.6 | 100 | 92.3 | 86.6 | 100 | 99.4 | 98.6 |
| 4 | 100 | 96.0 | 90.5 | 100 | 92.2 | 86.6 | 100 | 99.4 | 98.5 |
| 5 | 100 | 95.8 | 90.3 | 100 | 91.8 | 85.9 | 100 | 99.4 | 98.6 |
| 6 | 100 | 89.0 | 80.1 | 100 | 79.3 | 69.7 | 100 | 99.4 | 98.6 |
| 7 | 100 | 85.4 | 78.0 | 100 | 78.1 | 67.9 | 100 | 99.4 | 98.5 |

TABLE 35-continued

| No. | RP-HPLC (%) | | | IE-HPLC (%) | | | SE-HPLC (%) | | |
|---|---|---|---|---|---|---|---|---|---|
| | 0 weeks | 2 weeks | 4 weeks | 0 weeks | 2 weeks | 4 weeks | 0 weeks | 2 weeks | 4 weeks |
| 8 | 100 | 96.1 | 90.5 | 100 | 92.2 | 85.2 | 100 | 99.4 | 98.5 |
| 9 | 100 | 95.8 | 90.2 | 100 | 92.2 | 85.1 | 100 | 99.4 | 98.5 |
| 10 | 100 | 84.2 | 77.0 | 100 | 82.9 | 75.3 | 100 | 99.4 | 98.4 |
| 11 | 100 | 75.3 | 70.3 | 100 | 81.9 | 73.7 | 100 | 99.1 | 98.0 |
| 12 | 100 | 61.0 | 54.4 | 100 | 78.8 | 69.0 | 100 | 99.1 | 98.1 |

As can clearly be seen from the RP-HPLC and IE-HPLC results of Table 35, the stability of the long acting insulinotropic peptide conjugate was highest when the pH of the buffer was in the claimed range of 5.2 to 7.0. However, when the pH was 7.5 to 8.5, purity of the major peak decreased, whereas when the compositions were stored at 25° C. for three weeks at pH 3.5 to 4.5, precipitation in the formulation was observed.

Additionally, as the non-ionic surfactant, the stability of the long acting insulinotropic peptide conjugate was shown to be highest when 0.001% to 0.05% of polysorbate 20 was included in the liquid formulation. However, when 0.5% to 5.0% of polysorbate 20 was included, purity of the major peak decreased in a manner dependent on the concentration of polysorbate 20 in the RP-HPLC and IE-HPLC results.

Based on the above description, it will be apparent to those skilled in the art that various modifications and changes may be made without departing from the scope and spirit of the invention. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

What is claimed is:

1. A liquid formulation of a long-acting insulinotropic peptide conjugate, comprising:
    a pharmaceutically effective amount of the long-acting insulinotropic peptide conjugate wherein an insulinotropic peptide is linked to an immunoglobulin Fc region; and
    an albumin-free stabilizer, wherein the stabilizer comprises a buffer, a sugar alcohol, and a non-ionic surfactant,
    wherein the insulinotropic peptide is glucagon-like peptide-1, glucagon-like peptide-2, exendin-3, exendin-4, or imidazo-acetyl exendin-4;
    wherein the formulation has a pH of about 5.2 to about 7.0; and
    wherein the non-ionic surfactant has a concentration of about 0.001% (w/v) to about 0.05% (w/v).

2. The liquid formulation according to claim 1, wherein the immunoglobulin Fc region is an Fc region derived from IgG, IgA, IgD, IgE, or IgM.

3. The liquid formulation according to claim 2, wherein the immunoglobulin Fc region is a hybrid of domains of different origins derived from immunoglobulins selected from the group consisting of IgG, IgA, IgD, IgE, and IgM.

4. The liquid formulation according to claim 2, wherein the immunoglobulin Fc region is a dimer or multimer consisting of single-chain immunoglobulins composed of domains of the same origin.

5. The liquid formulation of according to claim 2, wherein the immunoglobulin Fc region is an IgG4 Fc region.

6. The liquid formulation according to claim 5, wherein the immunoglobulin Fc region is a human aglycosylated IgG4 Fc region.

7. The liquid formulation according to claim 1, wherein the insulinotropic peptide is linked to the immunoglobulin Fc region via a non-peptidyl polymer or a fusion protein.

8. The liquid formulation according to claim 7, wherein the non-peptidyl polymer is a polyethylene glycol.

9. The liquid formulation according to claim 7, wherein the non-peptidyl polymer is selected from the group consisting of a biodegradable polymer; a lipid polymer; chitins; hyaluronic acid; and a combination thereof, wherein said biodegradable polymer is selected from the group consisting of polypropylene glycol, a copolymer of ethylene glycol and propylene glycol, polyoxyethylated polyol, polyvinyl alcohol, polysaccharide, dextran, polyvinyl ethyl ether, polylactic acid, and polylactic-glycolic acid.

10. The liquid formulation according to claim 1, wherein the pharmaceutically effective amount of the long-acting insulinotropic peptide conjugate has a concentration of about 0.5 mg/mL to about 150 mg/mL.

11. The liquid formulation according to claim 1, wherein the pharmaceutically effective amount of the long-acting insulinotropic peptide conjugate has a concentration of about 4.0 mg/mL to about 50 mg/mL.

12. The liquid formulation according to claim 1, wherein the sugar alcohol is one or more selected from the group consisting of mannitol, sorbitol, and sucrose.

13. The liquid formulation according to claim 12, wherein a concentration of the sugar alcohol is about 3% (w/v) to about 15% (w/v) based on a total volume of the liquid formulation.

14. The liquid formulation according to claim 1, wherein the buffer is a citrate buffer, an acetate buffer, or a histidine buffer.

15. The liquid formulation according to claim 1, wherein the buffer is a citrate buffer.

16. The liquid formulation according to claim 15, wherein a concentration of the citrate is about 10 mM to about 100 mM based on a total volume of the liquid formulation.

17. The liquid formulation according to claim 15, wherein the citrate is present in a form of citric acid monohydrate.

18. The liquid formulation according to claim 1, wherein the pH range of the formulation is about 5.2 to about 6.0.

19. The liquid formulation according to claim 1, wherein the pH range of the formulation is about 5.4 to about 7.0.

20. The liquid formulation according to claim 1, wherein the pH of the formulation is adjusted by using HCl and/or NaOH.

21. The liquid formulation according to claim 1, wherein the non-ionic surfactant is polysorbate 80 or polysorbate 20.

22. The liquid formulation according to claim 1, wherein the stabilizer further comprises methionine.

23. The liquid formulation according to claim 22, wherein a concentration of the methionine is about 0.005% (w/v) to about 0.1% (w/v) based on a total volume of the liquid formulation.

24. The liquid formulation according to claim 1, wherein the stabilizer further comprises one or more substances selected from the group consisting of a sugar, a polyalcohol, and an amino acid.

25. The liquid formulation according to claim 1, further comprising one or more preservatives selected from the group consisting of m-cresol, phenol, and benzyl alcohol.

26. The liquid formulation according to claim 25, wherein a concentration of the one or more preservatives is about 0.001% (w/v) to about 1% (w/v) based on a total volume of the liquid formulation.

27. The liquid formulation according to claim 25, wherein the preservative is m-cresol.

28. A liquid formulation of a long-acting insulinotropic peptide conjugate, the liquid formulation comprising:
   a pharmaceutically effective amount of the long-acting insulinotropic peptide conjugate wherein an insulinotropic peptide is linked to an immunoglobulin Fc region via polyethylene glycol; and an albumin-free stabilizer, wherein the stabilizer comprises citrate buffer, mannitol, and polysorbate 20,
   wherein,
   the insulinotropic peptide is glucagon-like peptide-1, glucagon-like peptide-2, exendin-3, exendin-4, or imidazo-acetyl exendin-4;
   the formulation has a pH of about 5.2 to about 7.0; and
   the non-ionic surfactant has a concentration of about 0.001% (w/v) to about 0.05% (w/v).

29. The liquid formulation according to claim 28, wherein the stabilizer further comprises methionine.

30. A liquid formulation of a long-acting insulinotropic peptide conjugate, comprising:
   about 4 mg/mL, about 8.0 mg/mL, or about 12.0 mg/mL of the long-acting insulinotropic peptide conjugate wherein an insulinotropic peptide is linked to an immunoglobulin Fc region via polyethylene glycol;
   about 4.203 mg/mL citric acid monohydrate;
   about 0.1 mg/mL L-methionine;
   about 0.05 mg/mL polysorbate 20; and
   about 40 mg/mL D-mannitol;
   wherein
   the formulation has a pH of about 5.6, and the pH of the formulation is adjusted by using NaOH; and the insulinotropic peptide is imidazo-acetyl exendin-4.

31. A multiple-use liquid formulation of a long-acting insulinotropic peptide conjugate, the multiple-use liquid formulation comprising:
   a pharmaceutically effective amount of the long-acting insulinotropic peptide conjugate wherein an insulinotropic peptide is linked to an immunoglobulin Fc region;
   an albumin-free stabilizer, wherein the stabilizer comprises a buffer, a sugar alcohol, and a non-ionic surfactant; and
   one or more preservatives selected from the group consisting of m-cresol, phenol, and benzyl alcohol,
   wherein the insulinotropic peptide is glucagon-like peptide-1, glucagon-like peptide-2, exendin-3, exendin-4, or imidazo-acetyl exendin-4;
   wherein the formulation has a pH of about 5.2 to about 7.0; and
   wherein the non-ionic surfactant has a concentration of about 0.001% (w/v) to about 0.05% (w/v).

32. A method for preparing the liquid formulation of claim 1, the method comprising:
   mixing a long-acting insulinotropic peptide conjugate wherein an insulinotropic peptide is linked to an immunoglobulin Fc region with a stabilizer comprising a buffer, a sugar alcohol, and a non-ionic surfactant;
   wherein the insulinotropic peptide is glucagon-like peptide-1, glucagon-like peptide-2, exendin-3, exendin-4, or imidazo-acetyl exendin-4;
   wherein the buffer has a pH of about 5.2 to about 7.0; and
   wherein the non-ionic surfactant has a concentration of about 0.001% (w/v) to about 0.05% (w/v).

33. The method according to claim 32, wherein the stabilizer further comprises methionine and/or a preservative.

* * * * *